US011247020B2

(12) United States Patent
McCollum et al.

(10) Patent No.: US 11,247,020 B2
(45) Date of Patent: Feb. 15, 2022

(54) MANUAL RESUSCITATOR REGULATING SYSTEM

(71) Applicant: Fire Pencil LLC, Washougal, WA (US)

(72) Inventors: Bobbi Sue McCollum, Washougal, WA (US); Randall Huebner, Portland, OR (US)

(73) Assignee: Fire Pencil LLC, Washougal, WA (US)

( * ) Notice: Subject to any disclaimer, the term of this patent is extended or adjusted under 35 U.S.C. 154(b) by 1350 days.

(21) Appl. No.: 15/182,557

(22) Filed: Jun. 14, 2016

(65) Prior Publication Data
US 2016/0367781 A1     Dec. 22, 2016

Related U.S. Application Data

(60) Provisional application No. 62/181,717, filed on Jun. 18, 2015, provisional application No. 62/253,676, filed on Nov. 10, 2015.

(51) Int. Cl.
*A61M 16/20*     (2006.01)
*A61M 16/06*     (2006.01)
(Continued)

(52) U.S. Cl.
CPC ...... *A61M 16/201* (2014.02); *A61M 16/0078* (2013.01); *A61M 16/0084* (2014.02);
(Continued)

(58) Field of Classification Search
CPC ............ A61M 16/201; A61M 16/0084; A61M 16/0078; A61M 16/04; A61M 16/06;
(Continued)

(56) References Cited

U.S. PATENT DOCUMENTS 1,896,716 A    2/1933   McKesson
2,138,845 A    12/1938   Erickson
(Continued)

OTHER PUBLICATIONS

The U.S Receiving Office, International Search Report in International Application No. PCT/US16/37936, dated Sep. 8, 2016, 2 pages.
(Continued)

*Primary Examiner* — Tu A Vo
(74) *Attorney, Agent, or Firm* — Kolisch Hartwell, P.C.

(57) ABSTRACT

A manual resuscitator regulating system for regulating the rate and volume of ventilation during manual resuscitation. The manual resuscitator regulating system may include an intake assembly configured to permit a selected volume of gas to flow into a chamber over a predetermined amount of time and/or an outtake assembly configured to permit a selected volume of gas flow out of the chamber over a predetermined amount of time. The intake assembly and/or the outtake assembly may include one or more adjustment mechanisms configured to allow a user to selectively adjust volume. The intake assembly and the outtake assembly may be configured to coordinate with one another to deliver a selected tidal volume and/or volume of gas. The manual resuscitator regulating system may include a placement indicator configured to indicate or guide a user where to squeeze or compress the chamber.

20 Claims, 13 Drawing Sheets

(51) Int. Cl.
*A61M 16/00* (2006.01)
*A61M 16/04* (2006.01)
(52) U.S. Cl.
CPC ............. *A61M 16/04* (2013.01); *A61M 16/06* (2013.01); *A61M 2205/581* (2013.01); *A61M 2205/582* (2013.01); *A61M 2205/584* (2013.01); *A61M 2205/586* (2013.01)
(58) Field of Classification Search
CPC ...... A61M 2205/581; A61M 2205/582; A61M 2205/584; A61M 2205/586; A61M 16/021; A61M 16/0003; A61M 16/0051; A61M 2205/52; A61M 2205/075; A61M 2016/0033; A61M 2205/15; A61M 2205/8212; A61M 2205/502; A61M 2016/0036; A61M 2205/8206; A61M 2205/583; A61M 2016/0027; A61B 5/0935; A61B 5/087; A61B 5/085; G09B 23/288; A61H 31/00–008
See application file for complete search history.

(56) References Cited

U.S. PATENT DOCUMENTS

| | | | |
|---|---|---|---|
| 2,162,242 A | 6/1939 | Branower | |
| 2,408,136 A | 9/1946 | Fox | |
| 3,046,978 A * | 7/1962 | Lea | A61M 16/0084 128/205.13 |
| 3,356,100 A | 12/1967 | Seeler | |
| 3,726,274 A | 4/1973 | Bird et al. | |
| 3,874,378 A | 4/1975 | Isaacson et al. | |
| 4,077,404 A | 3/1978 | Elam | |
| 4,121,580 A | 10/1978 | Fabish | |
| 4,239,038 A | 12/1980 | Holmes | |
| 4,374,521 A | 2/1983 | Nelson et al. | |
| 4,934,360 A | 6/1990 | Heilbron et al. | |
| 5,140,982 A * | 8/1992 | Bauman | A61M 16/0078 128/205.11 |
| 5,301,667 A | 4/1994 | McGrail et al. | |
| 5,305,739 A * | 4/1994 | Gray | A61M 16/0078 128/205.13 |
| 5,398,714 A | 3/1995 | Price | |
| 5,400,779 A | 3/1995 | De Resende | |
| 5,497,767 A | 3/1996 | Olsson et al. | |
| 5,520,170 A | 5/1996 | Laswick et al. | |
| 5,520,173 A | 5/1996 | Kuhn | |
| 5,537,998 A | 7/1996 | Bauman | |
| 5,628,305 A * | 5/1997 | Melker | A61M 16/0048 128/202.29 |
| 5,632,298 A | 5/1997 | Artinian | |
| 5,787,880 A * | 8/1998 | Swanson | A61M 16/0084 128/202.28 |
| 5,787,882 A | 8/1998 | Hamilton | |
| 6,289,890 B1 | 9/2001 | Bliss et al. | |
| 6,609,518 B2 | 8/2003 | Lamb | |
| 6,718,979 B1 | 4/2004 | Britt et al. | |
| 6,745,769 B2 * | 6/2004 | Klempau | A61M 16/0078 128/205.13 |
| 6,776,160 B2 | 8/2004 | Wang | |
| 6,792,947 B1 | 9/2004 | Bowden | |
| 7,392,805 B2 | 7/2008 | Maguire | |
| 7,513,254 B2 | 4/2009 | Ben et al. | |
| 7,537,008 B2 | 5/2009 | Halpern | |
| 7,658,188 B2 | 2/2010 | Halpern et al. | |
| 7,980,244 B2 | 7/2011 | Boone et al. | |
| 8,151,790 B2 | 4/2012 | Lurie et al. | |
| 8,235,043 B2 | 8/2012 | Halpern | |
| 9,586,015 B1 * | 3/2017 | Lindner | A61M 16/0051 |
| 2006/0156823 A1 | 7/2006 | Lau et al. | |
| 2006/0272644 A1 | 12/2006 | Halpern | |
| 2007/0017521 A1 | 1/2007 | Ben et al. | |
| 2007/0169780 A1 | 7/2007 | Halpern et al. | |
| 2007/0267019 A1 | 11/2007 | Lugtigheid | |
| 2008/0053445 A1 * | 3/2008 | Kroupa | A61M 16/0078 128/205.23 |
| 2008/0115787 A1 | 5/2008 | Ingenito | |
| 2008/0314386 A1 * | 12/2008 | Myklebust | A61M 16/0078 128/205.15 |
| 2009/0241959 A1 | 10/2009 | Halpern | |
| 2010/0132709 A1 | 6/2010 | Halpern | |
| 2011/0120472 A1 * | 5/2011 | Lee | A61M 16/0075 128/205.14 |
| 2011/0168179 A1 | 7/2011 | Boone et al. | |
| 2011/0247623 A1 | 10/2011 | McCarthy | |
| 2012/0222677 A1 * | 9/2012 | Lee | A61M 16/0078 128/205.14 |
| 2012/0272965 A1 | 11/2012 | Halpern | |
| 2013/0125894 A1 | 5/2013 | Halpern | |
| 2013/0180527 A1 * | 7/2013 | Kim | A61M 16/0078 128/205.13 |
| 2014/0005566 A1 | 1/2014 | Homuth et al. | |
| 2014/0060543 A1 | 3/2014 | Howe, Jr. et al. | |
| 2014/0318544 A1 | 10/2014 | Murphy et al. | |
| 2014/0318545 A1 | 10/2014 | Ackerman et al. | |
| 2015/0238722 A1 * | 8/2015 | Al-Ali | A61M 16/085 128/205.13 |
| 2018/0021533 A1 * | 1/2018 | Gausche-Hill | A61M 16/0816 128/205.14 |

OTHER PUBLICATIONS

The U.S Receiving Office, Written Opinion of the International Searching Authority, in International Application No. PCT/US16/37936, dated Sep. 8, 2016, 5 pages.
The International Bureau of WIPO, International Preliminary Report on Patentability regarding PCT Patent Application No. PCT/US2016/037936, dated Dec. 28, 2017, 7 pages.
Aufderheide et al., Death by hyperventilaion: A common and life threatening problem during cardiopulmonary resuscitation, Journal of Critical Care Medicine, 2004, vol. 32, No. 9 (Supplemental), pp. S345-S351.
Aufderheide et al., Hyperventilation-Induced Hypotension During Cardiopulmonary Resuscitation, American Heart Association Journal, 2004, pp. 1960-1965.
Abella et al., Quality of Cardiopulmonary Resuscitation During In-Hospital Cardiac Arrest, The Journal of the American Medicine Association, 2005, vol. 293, No. 3, pp. 305-310.
Culbreth et al., Manual Bag Valve Mask Ventilation Performance Among Respiratory Therapists, Heart and Lung.
Hasegawa et al., Association of Prehospital Advanced Airway Management with Neurologic Outcome and Survival in Patients with Out-of-Hospital Cardiac Arrest,The Journal of American medical association, 2013, vol. 390, No. 3, pp. 257-266.
Losert et al., Quality of Cardiopulmonary Resuscitation Among Highly Trained Staff in an Emergency Department Setting, Arch Intern Med, 2006, vol. 166, pp. 2375-2380.
Link et al., Part 7: Adult Advanced Cardiovascular Life Support: 2015 American Heart Association Guidelines Update for Cadiopulmonary Resuscitation and Emergency Cardiovascular Care, Circulation, 2015, vol. 132, Supplemental 2, pp. S444-S464.
McInnes et al., The first quantitative report of ventilation rate during resuscitation of older children and adolescents. Resuscitation, 2011, vol. 82, No. 8, pp. 1025-1029.
Milander et al., Chest Compression and Ventilation Rates during Cardiopulmonary Resuscitation: The Effects of Audible Tone Guidance, Academic Emergency Medicine, 1995, vol. 2, No. 8, pp. 708-713.
Mondolfi et al., Comparison of self-inflating bags with anesthesia bags for bag-mask ventilation in the pediatric emergency department, Pediatric Emergency Care, 1997, vol. 13, No. 5, pp. 312-316.
Niebauer et al., Hyperventilation in Pediatric Resuscitation: Performance in Simulated Pediatric Medical Emergencies, 2011, Pediatrics, vol. 128, No. 5, 1195-1200.
O'Neill et al., Do we hyperventilate cardiac arrest patients? Resuscitation, 2006, vol. 73, pp. 82-85.

(56) References Cited

OTHER PUBLICATIONS

Weiler et al., Assessment of Pulmonary Mechanics and Gastric Inflation Pressure During Mask Ventilation, Prehospital Disaster Medicine, 1995, vol. 10, No. 2, pp. 52-56.

Maertens et al., Patients with cardiac arrest are ventilated two times faster than guidelines recommend: An observational prehospital study using tracheal pressure measurement, Resuscitation, 2013, vol. 84, No. 7, pp. 921-926.

Lavonas et. al., Highlights of the 2020 American Heart Association Guidelines for CPR and ECC, American Heart Association, 2020, 32 pages.

Panchal et al., 2019 American Heart Association Focused Update on Advanced Cardiovascular Life Support: Use of Advanced Airways, Vasopressors and Extracorporeal Cardiopulmonary Resuscitation During Cardiac Arrest: An Update to the American Heart Association Guidelines for Cardiopulmonary Resuscitation and Emergency Cardiovascular Care, Circulation, 2019, vol. 140, No. 24, pp. 881-894.

\* cited by examiner

MANUAL RESUSCITATOR REGULATING SYSTEM

CROSS REFERENCE TO RELATED APPLICATIONS

This application is based upon and claims priority to U.S. Provisional Patent Application Ser. No. 62/181,717, filed Jun. 18, 2015, and U.S. Provisional Patent Application Ser. No. 62/253,676, filed Nov. 10, 2015, each of which is hereby incorporated by reference.

FIELD OF INVENTION

This disclosure generally relates to a system for manual resuscitators. More specifically, it relates to systems and methods for regulating the rate and volume of ventilation during manual resuscitation.

INTRODUCTION

Manual resuscitators, also known as bag-valve-masks or BVMs, provide positive pressure ventilation to patients suffering from significant respiratory distress or failure. A manual resuscitator generally consists of a face mask connected to a re-inflating bag or chamber with an air/oxygen intake. Ventilation is delivered to the patient by maintaining a face-to-mask seal and performing manual compression of the chamber. In instances where an advanced airway is used, the manual resuscitator is connected directly to that airway.

Operating or using a manual resuscitator may include maintaining a face-to-mask seal and compressing the chamber until adequate chest rise is achieved. The chest rise may be a clinical indicator that appropriate tidal volume (or the air/oxygen required for a breath) has been attained. For an average adult, the appropriate tidal volume is approximately 500 ml for each breath (or respiration). The American Heart Association recommends that adults receive each respiration at a rate of 10-12 breaths per minute during respiratory failure and 8-10 breaths per minute during cardiac arrest with any advanced airway in place. Tidal volumes and respiratory rates can vary based on patient size, age and morbidity.

Currently, manual resuscitators that are used throughout the emergency and hospital settings have no monitoring system in place to ensure proper volumes and respiratory rate. The respiratory rate and tidal volumes may be entirely dependent on the operator of the manual resuscitator. Since the operator of a manual resuscitator can vary in skill, training, coordination, size, and strength, the respiratory rates and tidal volumes can vary and be inconsistent. For example, an operator's ability to time chamber compression, often without the benefit of a clock or timer, can vary. Additionally, different hand sizes may deliver different amounts of gas, for example, air, upon compression of the chamber. This can create variability in tidal volumes and deliver overall higher volumes, which may increase pulmonary pressure. Studies have shown that when manual resuscitators are used, adult patients are receiving an average of 18 breaths per minute up to 37 breaths per minute (Kohler, Losert, Sterz, 2006). Pediatric patients often have similar experiences, especially because pediatric patients have respiratory requirements that can vary significantly by age and size.

Excessive tidal volumes and respiratory rates can cause hyperventilation. Hyperventilation has been linked to increased intrathoracic pressures, lung tissue damage, decreased coronary perfusion pressures and reduced survival rates (Kohler, Losert, Sterz, 2006). Hyperventilation may also decrease neurological outcomes in post-cardiac arrest patients. Another cause of morbidity and mortality post cardiac/respiratory arrest can include aspiration pneumonia, which is often caused by an overflow of air and/or oxygen volume entering the stomach. This can lead to vomiting and resulting aspiration.

Furthermore, manual resuscitators are typically required during stressful conditions where a number of things must be done quickly and competently. For example, this may include performing chest compressions, inserting an intravenous catheter, and/or administrating emergency medications, in addition to delivering breaths via the manual resuscitator, which may include maintaining face-to-mask seal, watching for adequate chest rise, assessing for suctioning needs, and ensuring appropriate respiratory rate is maintained. Because of this, respiratory rate is often inaccurately timed and tidal volume may be excessive and delivered at inappropriate pressures.

To try and solve this problem, some manual resuscitators have a sliding piston between the chamber and the face mask, but the piston can allow a variable volume between a minimum and maximum amount and does not regulate respiratory rate. Additionally, some manual resuscitators include a timer to assist an operator in monitoring respiratory rate, but the timer may require constant auditory or visual monitoring which can be challenging to hear or focus on during a stressful situation. Furthermore, some manual resuscitators have been significantly redesigned to try and solve this problem, but these redesigns can result in increased manufacturing and consumer costs due to the complexity, as well as additional training.

Accordingly, a simple, dependable and cost-effective manual resuscitator design that can address the above challenges and preserve the existing advantages of a manual resuscitator is desired.

Examples of manual resuscitator systems are disclosed in U.S. Pat. Nos. 6,792,947 and 7,392,805 and U.S. Application Serial No. 2014/0318544. The disclosures of these and all other publications referenced herein are incorporated by reference in their entirety for all purposes.

SUMMARY OF THE INVENTION

The present disclosure provides a system for regulating the rate and volume of ventilation during manual resuscitation. A manual resuscitator regulating system may include an intake assembly configured to permit a selected volume of gas to flow into a chamber over a predetermined amount of time and/or an outtake assembly configured to permit a selected volume of gas flow out of the chamber over a predetermined amount of time. The intake assembly and/or the outtake assembly may include one or more adjustment mechanisms configured to allow a user to selectively adjust gas volume flow. The intake assembly and the outtake assembly may be configured to coordinate with one another to deliver a selected tidal volume and/or volume of gas. In some examples, the manual resuscitator regulating system may include a feedback mechanism configured to provide one or more signals to a user when to squeeze or compress the chamber. In some examples, the manual resuscitator regulating system may include a placement indicator configured to indicate or guide a user where to squeeze or compress the chamber.

DETAILED DESCRIPTION

Figure 1:
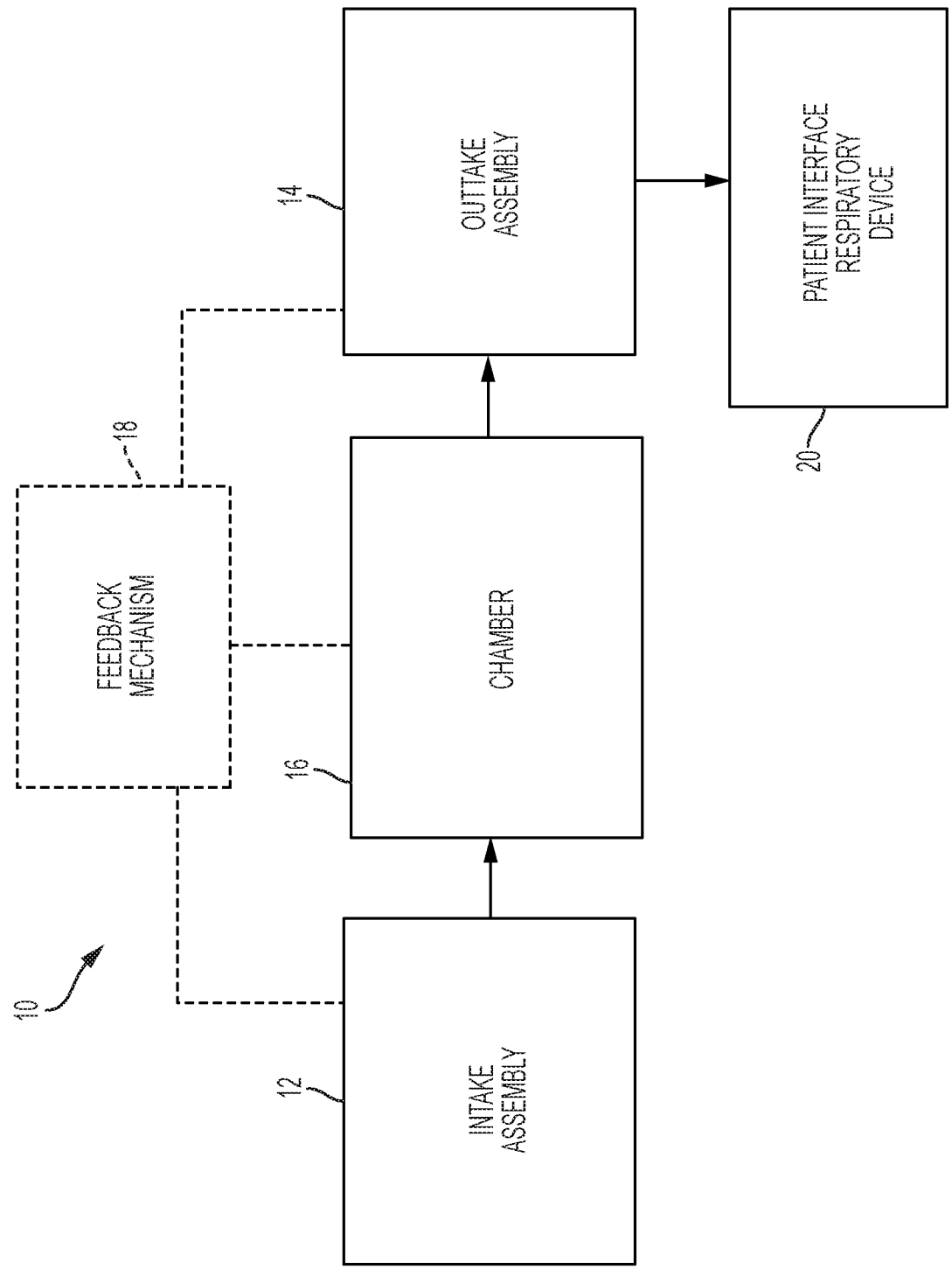
FIG. 1 is a block diagram of an embodiment of a manual resuscitator regulating system in accordance with the principles of the present disclosure.

FIG. 1 is a block diagram of a manual resuscitator regulating system, generally indicated at 10. Manual resuscitator regulating system 10 may include any suitable structure configured to regulate the rate and volume of ventilation during manual resuscitation. For example, manual resuscitator regulating system 10 may include a chamber 16, an intake assembly 12, an outtake assembly 14, and/or a patient interface respiratory device 20. In some examples, the manual resuscitator regulating system may additionally, or alternatively, include a feedback mechanism 18. The manual resuscitator regulating system may be configured to attach to and/or incorporate with other manual resuscitators. For example, one or more components and/or structures of the manual resuscitator regulating system, such as the intake assembly and/or the outtake assembly, may be included, incorporated and/or retrofitted on to a pre-existing manual resuscitator.

Chamber 16 may be made of one or more suitable materials, such as rubber, plastic, and/or other materials with resilient properties. Chamber 16 may be configured to receive and/or retain gas, such as during a refill, and expel gas when a user compresses or squeezes the chamber. The chamber may be configured to regain its original shape after a user compresses or squeezes the chamber. The chamber may be any suitable size(s) or shape(s) to facilitate and/or support one or more components of the manual resuscitator regulating system. For example, the chamber may be sized to retain a predefined maximum volume of gas. In some examples, the chamber may be configured to retain a volume of approximately 1000 ml to 2,100 ml. In other examples, the chamber may be configured to retain a volume of approximately 500 ml. Chamber 16 may be shaped to help a user engage and/or compress the chamber with one and/or two hands. In some examples, the chamber may be shaped to provide an ergonomic fit for a user's hands. In other examples, the chamber may be configured to indicate or guide a user where to squeeze or compress the chamber, such as a placement indicator. Additionally, or alternatively, the chamber may be configured to help a user hold and/or support the chamber, such as by including non-slip gripping material and/or a strap that can be engaged by a user's hand(s).

Chamber 16 may extend between intake assembly 12 and outtake assembly 14. Chamber 16 may be configured to receive gas from intake assembly 12 and expel gas from the chamber through outtake assembly 14. Chamber 16 may attach to intake assembly 12 and/or outtake assembly 14. In some examples, the chamber may include one or more structures configured to attach the chamber to one or more components and/or structures of the intake assembly and/or the outtake assembly. In other examples, the intake assembly and/or the outtake assembly may be releasably attached to the chamber. This may help facilitate the removal or replacement of the intake assembly and/or the outtake assembly. Chamber 16 may include any suitable structure configured to form or facilitate an air tight seal between the chamber and the intake assembly and/or the outtake assembly.

Intake assembly 12 may include any suitable structure configured to permit a selected volume of gas to flow into the chamber over a predetermined amount of time. For example, intake assembly 12 may include one or more valves, ports, discs, walls, plates, chambers, apertures, springs, seals, levers, and elastic bands, among others. In some examples, one or more of the above described structures may be configured to permit approximately 600 ml to flow in the chamber over a five (5) second period. In other examples, one or more of the above structures may be configured to permit approximately 450 ml to flow in the chamber over a three (3) second period. Additionally, the intake assembly may include one or more valves, or similar structures, to permit gas to flow in one direction.

This configuration may serve to help reduce the volume and/or rate of gas delivered to a patient and help provide a more consistent and controlled volume and/or rate delivered. For example, the volume and rate of gas that enters the chamber may be limited and/or slowed to a predetermined amount of time (e.g. five seconds) such that if a user compresses or squeezes the chamber prior to the predetermined amount of time, the user may be prevented from delivering a full tidal volume because the chamber has not reached the selected volume of gas. This in turn may help reduce the overall volume delivered to the patient. Additionally, the slowed rate of gas entering the chamber may serve to help signal and/or provide feedback, as part of a feedback mechanism 18, to the user when to compress the chamber and deliver another breath to the patient, as described below in more detail.

Intake assembly 12 may be configured to allow a user to select, adjust, and/or toggle settings of the intake assembly.

For example, the intake assembly may include one or more adjustment mechanisms configured to allow a user to selectively adjust the volume permitted to flow into chamber 16. Intake assembly 12 may include any suitable structure to allow a user to select, adjust, and/or toggle between at least two volume amounts and/or settings. In some examples, the intake assembly may include one or more levers, buttons, dials, switches, and/or other suitable devices. In other examples, the intake assembly may be configured to allow a user to turn off or disable some or all of the functions of the intake assembly, such as an override setting.

Intake assembly 12 may be configured to coordinate with and/or support one or more components of outtake assembly 14. For example, intake assembly 12 may be configured to coordinate with outtake assembly 14 to deliver a selected volume of gas, such as the tidal volume delivered to a patient. In some examples, one or more settings on the intake assembly may be configured to coordinate with and/or complement one or more settings on the outtake assembly to deliver a selected volume amount to a patient. In other examples, the intake assembly and the outtake assembly may be configured to deliver a selected tidal volume when a setting on the intake assembly is the same as a setting on the outtake assembly. Additionally, the intake assembly and the outtake assembly may be configured to deliver a selected tidal volume at a selected pressure. For example, the intake assembly and the outtake assembly may be configured to deliver a selected tidal volume at an increased pressure when a setting on the intake assembly is different than a setting on the outtake assembly. This may help deliver gas to a patient with decreased lung compliance. The intake assembly may include the same structures as the outtake assembly. In other examples, the intake assembly may include one or more different structures in relation to the outtake assembly.

Intake assembly 12 may include one or more references, indices, guides, symbols, and/or codes to help assist a user to select, adjust, and/or toggle settings of the intake assembly. The settings on the intake assembly may be configured for various ages and/or sizes of a patient, including adult, pediatric, and infant patients. For example, the intake assembly may include one or more numbers, colors, and/or letters configured to represent the volume of gas that may flow into the chamber when selected. In some examples, the intake assembly may include one or more numbers representing the tidal volume that may be delivered to the patient when selected. In other examples, the intake assembly may include one or more colors that correspond to the age and/or size of a patient, and when selected, may deliver a predetermined volume and/or tidal volume that is commensurate with the age and/or average size of the patient. In some examples, the intake assembly may include one or more colors that correspond to the color coding schemes of existing resuscitation systems such as, but not limited to, the Broselow-Luten system.

Intake assembly 12 may be operably connected to one or more sources of gas, including for example, an oxygen reservoir, an oxygen tank, and/or ambient air, and/or other gas composition(s). The intake assembly may include any suitable structure configured to receive and/or attach to a hose, tubing, or other similar structure. Intake assembly 12 may be made of one or more suitable materials, such as plastics, rubbers, textiles, metals, vinyls, foams, latexes, and/or other materials. Intake assembly 12 may be any suitable shape(s) and dimension(s) to facilitate and/or support one or more components of manual resuscitator regulating system 10.

Outtake assembly 14 may include any suitable structure configured to permit a selected volume of gas to flow out of the chamber over a predetermined amount of time. For example, outtake assembly 14 may include one or more valves, ports, discs, walls, plates, chambers, apertures, springs, seals, levers, and elastic bands, among others. In some examples, one or more of the above described structures may be configured to permit approximately 600 ml to flow out of the chamber over a one (1) second period. In other examples, one or more of the above structures may be configured to permit approximately 450 ml to flow out of the chamber over a one (1) second period. Additionally, the outtake assembly may include one or more valves, or similar structures, to permit gas to flow in one direction.

This configuration may serve to help reduce the volume and/or rate of gas delivered to a patient and help provide a more consistent and controlled volume and/or rate delivered. For example, the volume and rate of gas that exits the chamber may be limited and/or slowed such that the physical compression of the chamber may be limited and/or slowed. This in turn may help prevent a user from delivering a selected volume of gas faster than a predetermined amount of time (e.g. one second), which may help reduce the overall volume delivered to the patient. Additionally, the slowed rate of gas delivered to the patient may serve to help moderate pressure(s) of the gas delivered to a patient.

Outtake assembly 14 may be configured to allow a user to select, adjust, and/or toggle settings of the outtake assembly. For example, the outtake assembly may include one or more adjustment mechanisms configured to allow a user to selectively adjust the volume permitted to flow out of chamber 16. Outtake assembly 14 may include any suitable structure to allow a user to select, adjust, and/or toggle to between at least two volume amounts and/or settings. In some examples, the outtake assembly may include one or more levers, buttons, dials, switches, and/or other suitable devices. In other examples, the outtake assembly may be configured to allow a user to turn off or disable some or all of the functions of the outtake assembly, such as an override setting.

Outtake assembly 14 may be configured to coordinate with and/or support one or more components of intake assembly 12. For example, outtake assembly 14 may be configured to coordinate with intake assembly 12 to deliver a selected volume of gas, such as the tidal volume delivered to a patient. In some examples, one or more settings on the outtake assembly may be configured to coordinate with and/or complement one or more settings on the intake assembly to deliver a selected volume amount to a patient. In other examples, the outtake assembly and the intake assembly may be configured to deliver a selected tidal volume when a setting on the outtake assembly is the same as a setting on the intake assembly. Additionally, the intake assembly and the outtake assembly may be configured to deliver a selected tidal volume at a selected pressure. For example, the intake assembly and the outtake assembly may be configured to deliver a selected tidal volume at an increased pressure when a setting on the intake assembly is different than a setting on the outtake assembly. This may help deliver gas to a patient with decreased lung compliance. The outtake assembly may include the same structures as the intake assembly. In other examples, the outtake assembly may include one or more different structures in relation to the intake assembly.

Outtake assembly 14 may include one or more references, indices, guides, symbols, and/or codes to help assist a user to select, adjust, and/or toggle settings of the outtake assembly. The settings on the outtake assembly may be configured for various ages and/or sizes of a patient, including adult, pediatric, and infant patients. For example, the outtake assembly may include one or more numbers, colors, and/or letters configured to represent the volume of gas that may flow into the chamber when selected. In some examples, the outtake assembly may include one or more numbers representing the tidal volume that may be delivered to a patient when selected. In other examples, the outtake assembly may include one or more colors that correspond to the age and/or size of a patient, and when selected, may deliver a predetermined volume and/or tidal volume that is commensurate with the age and/or average size of the patient. In some examples, the outtake assembly may include one or more colors that correspond to the color coding schemes of existing resuscitation systems such as, but not limited to, the Broselow-Luten system.

Outtake assembly 14 may be attached and/or operably connected to patient interface respiratory device 20. The patient interface respiratory device is configured to deliver gas to a patient and may include a mask, endotracheal tube, laryngeal mask airway, etc. The outtake assembly may include any suitable structure configured to receive and/or attach to a hose, tubing, or other similar structure. Outtake assembly 14 may be made of one or more suitable materials, such as plastics, rubbers, textiles, metals, vinyls, foams, latexes, and/or other materials. Outtake assembly 14 may be any suitable shape(s) and dimension(s) to facilitate and/or support one or more components of manual resuscitator regulating system 10.

In some examples, manual resuscitator regulating system 10 may include a feedback mechanism 18, which may be configured to provide a user visual, audio, and/or tactile feedback. For example, chamber 16 may transition between a deflated state to a fully inflated state, whereby the fully inflated state may indicate and/or signal to a user through visual and/or tactile feedback that the selected amount of gas has entered the chamber and that the chamber may and/or should be compressed. In some examples, feedback mechanism 18 may be configured to provide a visual alarm, a sound alarm, and/or other suitable alarms to indicate when the chamber may be compressed. In other examples, feedback mechanism 18 may include one or more light sources configured to emit light and/or change colors to indicate when the chamber may or should be compressed by the user. The feedback mechanism may be operably connected to the chamber, intake assembly, and/or outtake assembly. For example, a setting on the intake assembly may be configured to permit an approximate gas flow into the chamber such that it takes approximately five seconds for the chamber to completely refill after compressing the chamber for about one second. The user receives a tactile signal from the refilled chamber that it is time to administer another one second compression, followed again by a five second refill phase. Alternatively, it may be desirable for some patients to adjust the intake and/or outtake valve(s) so that the ratio of intake time ($I_t$) to outtake time ($O_t$) is greater or less than 5:1 depending on the circumstances. For example, an optimal $I_t$::$O_t$ for a pediatric or infant patient may depend on size and intubation status.

Figure 2:
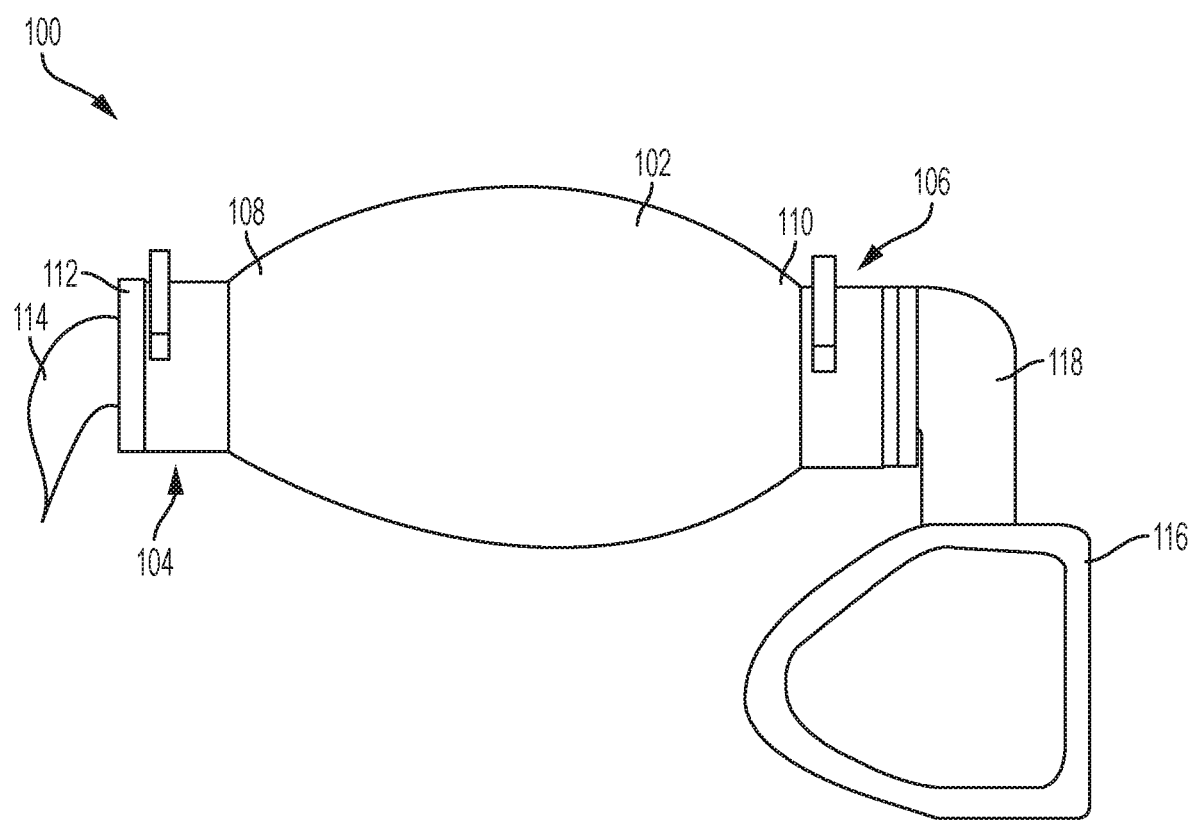
FIG. 2 is side elevation view of an embodiment of the manual resuscitator regulating system of FIG. 1.

FIGS. 2-6 show an embodiment of a manual resuscitator regulating system, which is generally indicated at 100, according to aspects of the present teachings. FIG. 2 depicts manual resuscitator regulating system 100 including a chamber 102 with a first end 108 and a second end 110, an intake assembly generally indicated at 104, and an outtake assembly generally indicated at 106. Intake assembly 104 is attached to first end 108 of the chamber. Outtake assembly 106 is attached to second end 110 of the chamber. Intake assembly 104 is operably attached and/or connected to a gas connector 112 and hosing 114. In other embodiments, intake assembly 104 may be operably attached and/or connected to other gas sources and/or structures. Outtake assembly 106 is operably connected and/or attached to a mask 116 through a mask connector 118. In other embodiments, outtake assembly 106 may be operably connected and/or attached to other alternative airways, such as an endotracheal tube or laryngeal mask airway. Each of intake assembly 104 and outtake assembly 106 has a one-way valve device only allowing gas to flow into the chamber through intake assembly 104 and out of the chamber through outtake assembly 106.

Figure 3:
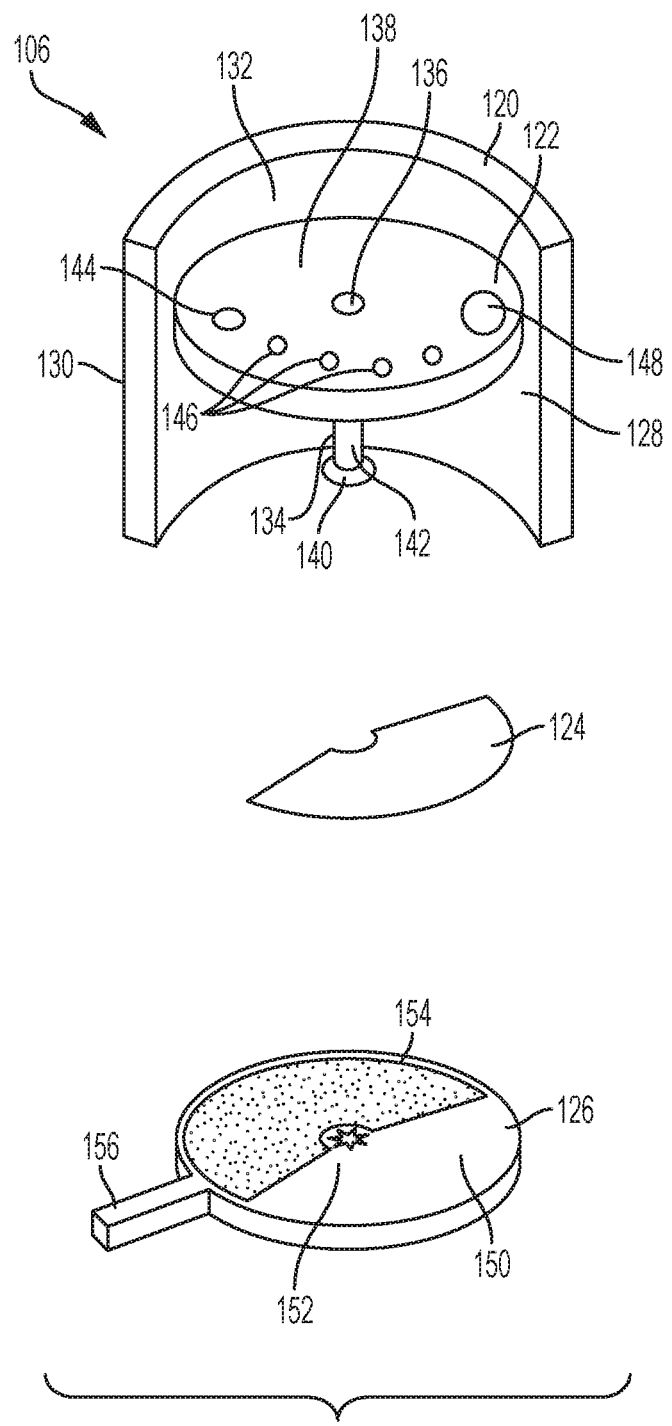
FIG. 3 is an exploded partially cut-away view of an outtake assembly of the manual resuscitator regulating system embodiment of FIG. 2, with valve housing material removed for clarity.

FIG. 3 is an exploded view of outtake assembly 106 of manual resuscitator regulating system 100 with valve housing material removed for clarity. Although FIGS. 3-6 depict an outtake assembly, except as indicated below, intake assembly 104 of manual resuscitator regulating system 100 may include the same and/or similar structures, components, and functions of outtake assembly 106. Outtake assembly 106 includes a valve housing 120, a regulator disc 122, a seal 124, and a control disc 126. Additionally, outtake assembly 106 may include and/or incorporate a flapper valve or a one-way valve (not shown) to facilitate one-way movement of gas. For example, the flapper valve may facilitate one-way movement of gas from chamber 102 to mask 116 in the outtake assembly and facilitate one-way movement of gas from gas connector 112 and/or hosing 114 to chamber 102 in the intake assembly. The flapper valve may be attached to and/or adjacent to the regulator disc.

Figure 6:
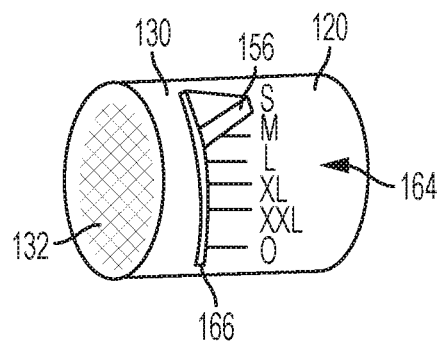
FIG. 6 is an isometric view of the valve housing of the manual resuscitator regulating system embodiment of FIG. 2, showing an index on the outer surface of the valve housing.

Valve housing 120 is configured to enclose and/or contain the regulator disc, the sealer, and the control disc. Valve housing 120 has an inner surface 128 and an outer surface 130 defining an opening 132 configured to facilitate the movement of gas through the valve housing to and/or from one or more components of the manual resuscitator regulating system. In other embodiments, valve housing 120 may partially enclose and/or contain more or less components of outtake assembly 106. Although FIGS. 3 and 6 depict a generally tubular valve housing, the valve housing may have any suitable size(s) or shape(s) to support the outtake assembly and/or other components of the manual resuscitator regulating system.

Valve housing 120 may be configured and/or oriented to position regulator disc 122 further away from or closer to chamber 102 in relation to control disc 126. For example, the valve housing of the outtake assembly may be oriented to position regulator disc 122 further away from chamber 102 in relation to control disc 126, and a valve housing of the intake assembly may be oriented to position a regulator disc adjacent or closer to chamber 102 in relation to a control disc, such that the valve housing of the outtake assembly and the valve housing of the intake assembly are oriented in the same direction in relation to the chamber. More specifically, when gas moves from gas connector 112 to chamber 102, the gas first flows to and/or through the control disc then to and/or through the regulator disc in the intake assembly, and when gas moves from chamber 102 to mask connector 118, the gas first flows to and/or through the control disc then to and/or through the regulator disc in the outtake assembly. In other examples, the valve housing of the outtake assembly and the valve housing of the intake assembly may be oriented in a different direction.

Regulator disc 122 includes a baseline aperture 144, at least one subsequent aperture 146, and an override aperture 148 disposed on a body 138 of the regulator disc. The baseline aperture and/or subsequent apertures are configured to permit a selected volume of gas through each aperture for a predetermined amount of time. Baseline aperture 144 is sized to permit a baseline or minimum amount of volume of gas through the baseline aperture for a predetermined amount of time. Subsequent apertures 146 are sized to permit an additional volume of gas through each aperture. Override aperture 148 is configured to disable some or all of the functions of the outtake assembly and/or manual resuscitator regulating system. For example, override aperture 148 may be sized to permit a maximum amount of gas through the override aperture.

The regulator disc in the outtake assembly may have a larger baseline aperture and/or larger subsequent apertures in relation to a baseline aperture and/or subsequent apertures in a regulator disc in the intake assembly. For example, the baseline aperture in the outtake assembly may be sized to permit approximately 400 ml of gas over a one (1) second time period and each subsequent aperture may be sized to permit approximately 100 ml of gas over a one (1) second period. In the intake assembly, the baseline aperture may be sized to permit approximately 400 ml of gas over a five (5) second time period and each subsequent aperture may be sized to permit approximately 100 ml of gas over a five (5) second period. Additionally, the override aperture in the outtake assembly may have a different size and/or shape in relation to an override aperture in the intake assembly.

Each subsequent aperture 146 may be a different size or shape. In some examples, each subsequent aperture 146 may be the same size and shape. In this embodiment, there is one (1) baseline aperture, four (4) subsequent apertures, and one (1) override aperture, but regulator disc 122 may have any suitable number of baseline apertures, subsequent apertures, and/or override apertures. Furthermore, in some embodiments, the outtake assembly and/or intake assembly may include at least one aperture configured to adjustable open and/or close.

Regulator disc 122 may be fixedly attached to inner surface 128 of valve housing 120. Regulator disc includes an attachment member 134 disposed in a central aperture 136 of body 138 of the regulator disc. The attachment member extends generally perpendicular from the body of the regulator disc and is configured to attach and/or connect to control disc 126. Attachment member 134 includes an annular collar 140 disposed on a distal end 142 of the attachment member. Annular collar 140 may be any suitable shape and size to facilitate attachment and/or connection to the control disc. In some examples, the annular collar may have a diameter approximately equal to or slightly greater than the diameter of the distal end of attachment member 134. Control disc 126 includes a body 150, a protrusion 152, a vent 154, and an adjustment arm 156. Control disc 126 is configured to rotate in relation to regulator disc 122 to expose and/or conceal the baseline aperture, subsequent apertures, and/or override aperture. Protrusion 152 is disposed on body 150 of the control disc and is configured to attach and/or connect to attachment member 134 to facilitate rotational movement of the control disc in relation to the regulator disc. Vent 154 may be sized to selectively conceal and/or expose baseline aperture 144, one or more subsequent apertures 146, and/or override aperture 148. Subsequent apertures 146 and baseline aperture 144 may be positioned on the regulator disc to allow vent 154 on the control disc to expose the baseline aperture and conceal and/or expose one or more subsequent apertures when the control disc is rotated in relation to the regulator disc. The vent on the control disc may be sized to expose all subsequent apertures 146 and baseline aperture 144 at a predetermined position of the control disc in relation to the regulator disc. In some embodiments, the vent on the control disc may be sized to expose baseline aperture 144 and all subsequent apertures 146 at a predetermined position of the control disc in relation to the regulator disc while concealing the override aperture.

Adjustment arm 156 on control disc 126 extends away from body 150 of the control disc. The adjustment arm is configured to allow a user to selectively rotate the control disc to a desired position in relation to the regulator disc. The adjustment arm may have any suitable shape(s) or size(s) to facilitate selecting, adjusting, and/or toggling between one or more apertures on the regulator disc, volume amounts, and/or settings.

Seal 124 is configured to facilitate and/or support sealing one or more of the subsequent apertures, the baseline aperture, and/or the override aperture. Seal 124 may be configured to prevent and/or limit gas from flowing through the covered and/or concealed apertures. Seal 124 may be attached to body 150 of the control disc adjacent to vent 154 substantially covering the body of the control disc. The seal may be sized to subtend less than 360 degrees to facilitate movement of gas through the vent. The seal may be made of any suitable materials, such as foams or plastics, among others, to facilitate an air tight seal.

Figure 4:
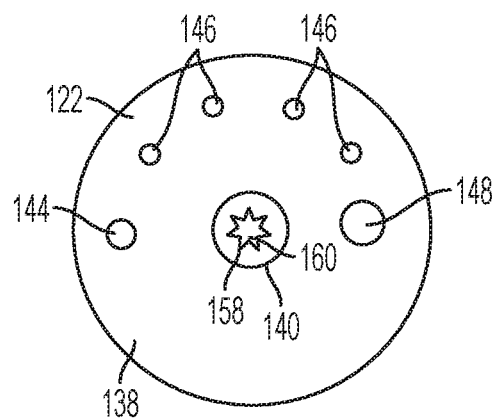
FIG. 4 is a bottom view of the regulator disc of the outtake assembly of the manual resuscitator regulating system embodiment of FIG. 2.
Figure 5:
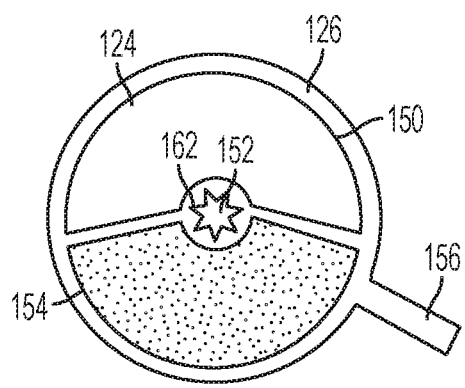
FIG. 5 is a top view of the control disc of the outtake assembly of the manual resuscitator regulating system embodiment of FIG. 2.

FIGS. 4-5 depict various views of regulator disc 122 and control disc 126 of the outtake assembly of manual resuscitator regulating system 100. As shown in FIG. 4, annular collar 140 of attachment member 134 may have teeth 158 formed on an internal surface 160 of the annular collar. The teeth may be configured to engage with complementary teeth 162 on protrusion 152 on the control disc. In other embodiments, the annular collar and/or attachment member may have any suitable shape(s) and size(s) to attach and/or engage with the control disc. As shown in FIG. 5, seal 124 is attached to control disc 126 and positioned adjacent vent 154.

FIG. 6 is an isometric view of valve housing 120 of the outtake assembly of manual resuscitator regulating system 100. Valve housing 120 includes an index 164 on outer surface 130 of the valve housing. Adjustment arm 156 is disposed in a slot 166 of the valve housing extending away from the valve housing. The slot may have any suitable shape(s) or size(s) to facilitate and/or support a user to selectively move the adjustment arm to one or more positions or settings.

Index 164 may include a series of letters, numbers, colors, codes, among others, corresponding with the position of adjustment arm 156 of control disc 126. For example, the index of the outtake assembly may include an "s" or "small" setting that is configured to be positioned to permit a selected volume of gas (e.g. 400 ml) over a one (1) second period of time. In the intake assembly, the index may include an "s" or "small" setting that is configured to be positioned to permit a selected volume of gas (e.g. 400 ml) over a five (5) second period of time. In some examples, the index of intake assembly may include an "s" or "small" setting that is configured to be positioned to permit a selected volume of gas (e.g. 400 ml) over a three (3) second period of time. The intake assembly and the outtake assembly may be configured to coordinate and/or complement the other, such that when both are adjusted to be on the same setting (e.g. small, 400 ml, blue, etc.), the intake assembly permits a selected volume of gas to allow the outtake assembly to permit a selected volume of gas (e.g. 400 ml) to be delivered to the patient. In some examples, when both the intake assembly and the outtake assembly are adjusted to be on the override setting (e.g. both set to "0"), the intake assembly and the outtake assembly permit a predetermined maximum amount of volume of gas to be delivered to the patient, such that the intake assembly and outtake assembly are disabled.

Figure 7:
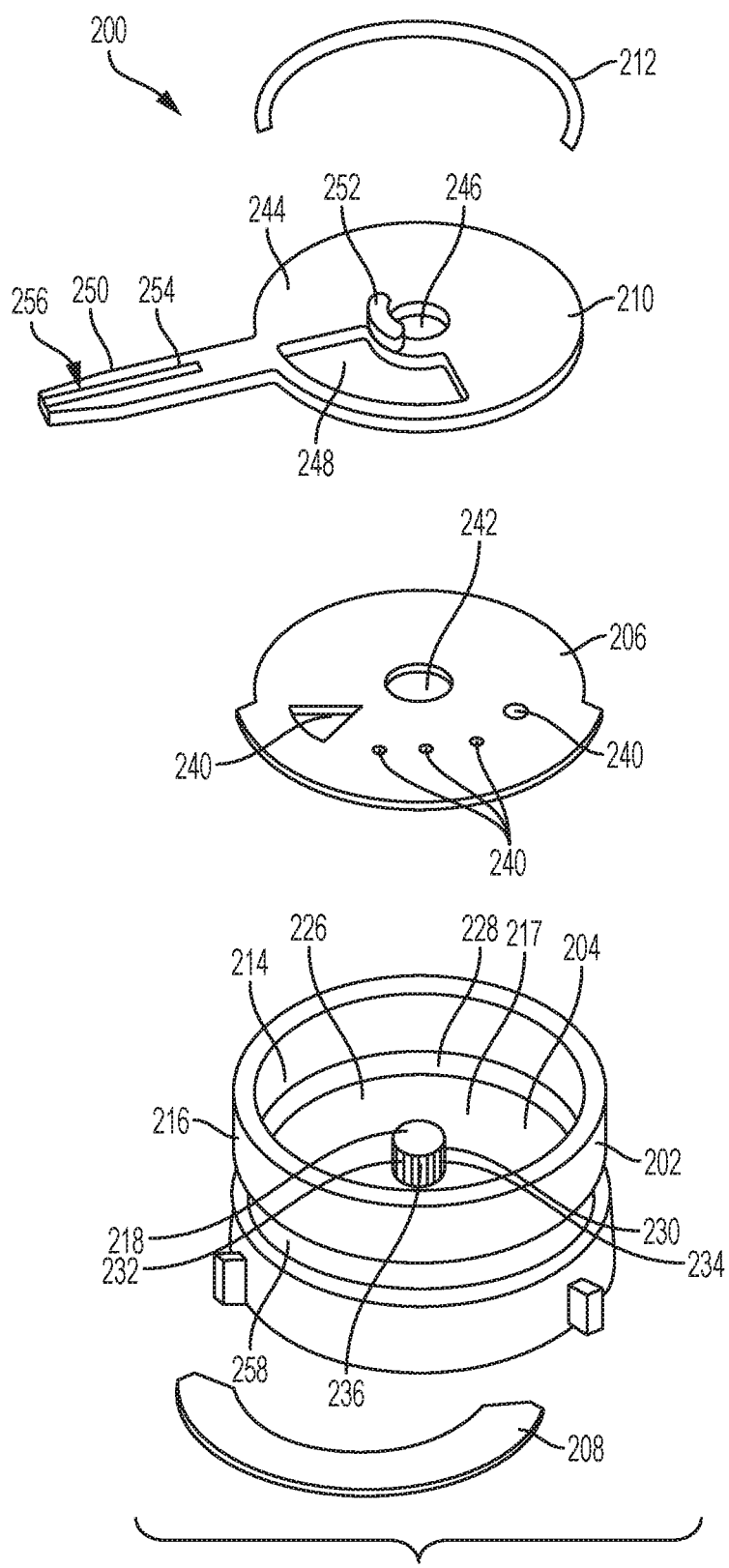
FIG. 7 is an exploded view of another embodiment of an outtake assembly of a manual resuscitator regulating system.
Figure 8:
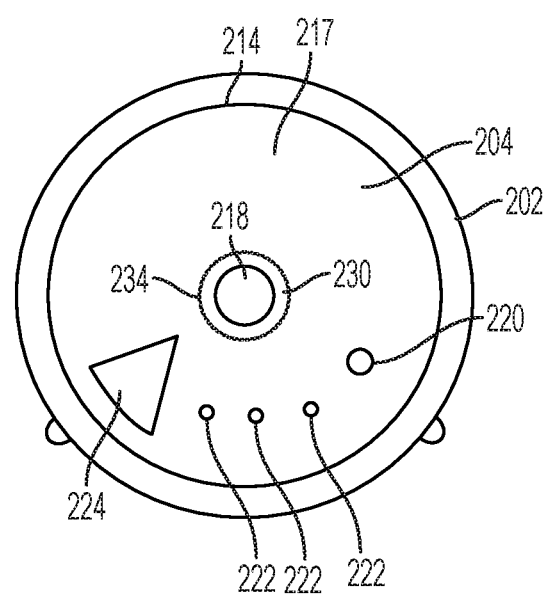
FIG. 8 is a top view of the valve housing of FIG. 7 showing the regulator disc attached therein.
Figure 9:
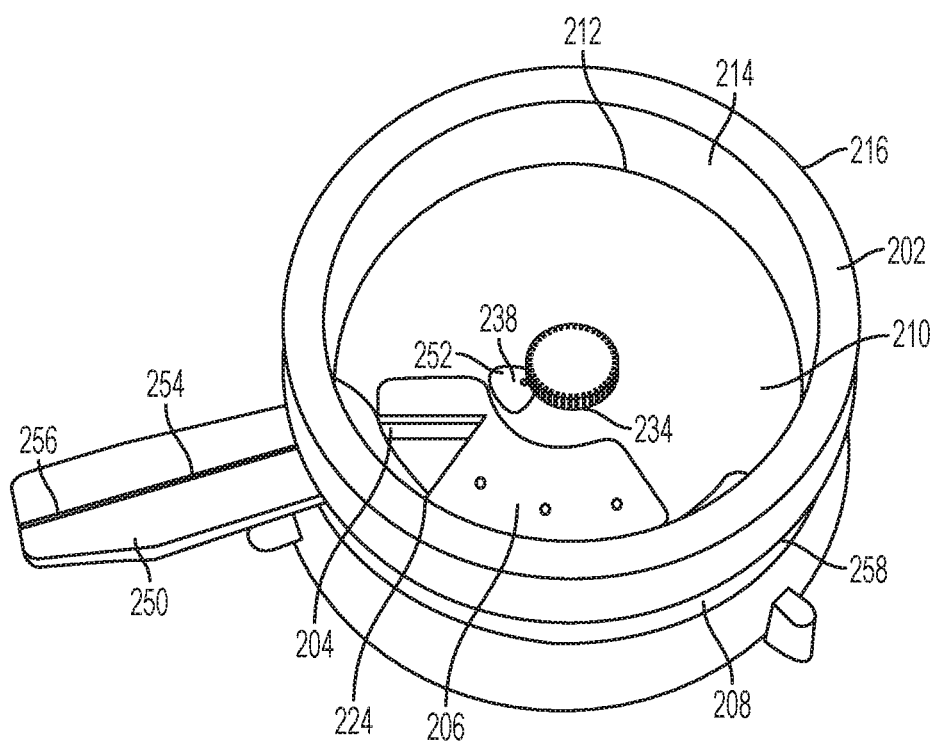
FIG. 9 is perspective view of the outtake assembly of FIG. 7.

FIGS. 7-9 show another embodiment of an outtake assembly of a manual resuscitator regulating system, which is generally indicated at 200, according to aspects of the present teachings. FIG. 7 is an exploded view of outtake assembly 200 and depicts outtake assembly 200 including a valve housing 202, a regulator disc 204, a first seal 206, a second seal 208, a control disc 210, and a fastener 212. FIG. 8 is a top view of valve housing showing regulator disc 204 attached within valve housing 202, and FIG. 9 is a perspective view of outtake assembly 200. Most of the features of this embodiment may be the same or similar to one or more embodiments described above and shown in FIGS. 1-6. For example, regulator disc 204 may have a body 217, an attachment member 218, a baseline aperture 220, at least one subsequent aperture 222, and an override aperture 224. Additionally, although FIGS. 7-9 depict an outtake assembly, an intake assembly, except as indicated below, may include the same and/or similar structures, components, and functions of outtake assembly 200.

Valve housing 202 has an inner surface 214 and an outer surface 216 defining an opening 226. Inner surface 214 forms a slotted groove 228 extending along the inner surface configured to receive and/or secure fastener 212. The slotted groove may be any suitable shape or size to receive and/or secure fastener 212 to and/or within the valve housing. In some examples, the slotted groove may be defined by inner surface 214 and regulator disc 204. Fastener 212 is configured to secure and/or retain one or more components of the outtake assembly to and/or within valve housing 202. For example, the fastener may be configured to secure and retain control disc 210 and/or seal 206 within the valve housing adjacent to regulator disc 204. This configuration may also serve to help facilitate an airtight seal between the control disc and regulator disc. Although FIG. 7 portrays the fastener to be substantially C-shaped, other shapes and dimensions may be appropriate depending on the size and shape of the slotted groove and/or valve housing.

Regulator disc 204 may be attached and/or incorporated to inner surface 214 of valve housing 202. Baseline aperture 220, subsequent apertures 222, and override aperture 224 are disposed on body 217 of the regulator disc. Attachment member 218 extends substantially perpendicular to the body of the regulator disc and is configured to receive first seal 206 and/or control disc 210. Attachment member includes an annular collar 230 on a distal end 232 of the attachment member and is configured to facilitate rotational movement of control disc 210 in relation to the regulator disc. The annular collar may rotate independently of the body of the regulator disc to allow the control disc to rotate while regulator disc remains in a fixed position in relation to the control disc. Annular collar 230 may include teeth 234 formed on an outer surface 236 of the annular collar and configured to engage with complementary teeth 238 on control disc 210. In some examples, the regulator disc and/or annular collar may be configured to variably resist the rotation of the control disc, such as a saw tooth clicking mechanism.

First seal 206 is configured to prevent and/or limit gas from flowing through and/or between the regulator disc, control disc, and/or valve housing. First seal 206 includes complementary apertures 240 shaped and sized to substantially resemble and correspond with the baseline aperture, subsequent apertures, and override aperture of the regulator disc. First seal 206 has a central aperture configured to engage with attachment member 218 of the regulator disc. The first seal may be attached to the body of the regulator disc substantially covering the body of the regulator disc. In some examples, the first seal may be physically separated from the regulator disc.

Control disc includes a body 244, a central hole 246, a vent 248, and an adjustment arm 250. Control disc is configured to rotate in relation to regulator disc 204 to expose and/or conceal the baseline aperture, subsequent apertures, and/or override aperture. Central hole 246 is configured to receive attachment member 218 of regulator disc 204. A protuberance 252 is disposed on body 244 of the control disc adjacent to the central hole. Protuberance 252 has complementary teeth 238 configured to engage with teeth 234 of the attachment member. Although FIGS. 7 and 9 depict two complementary teeth on the protuberance of control disc, the protuberance and/or body of control disc may include one, three, four, or more complementary teeth. Adjustment arm 250 defines a longitudinal recess 254 extending to a notch 256. The longitudinal recess may be configured to align with one or more letters, numbers, colors, codes, etc. on the outer surface of valve housing 202 (not shown), to facilitate a user to select one or more settings and/or positions. The adjustment arm may include any suitable structure(s), shape(s), or indicator(s) to facilitate a user to select one or more settings and/or positions. For example, the adjustment arm may include one or more symbols or shapes, such as arrows, dots, colors, triangles, etc. affixed on the adjustment arm.

Valve housing forms a slot 258 configured to receive adjustment arm 250 of control disc 210. The slot may have any suitable shape(s) or size(s) to facilitate a user to selectively move the adjustment arm to one or more positions or settings. Additionally, slot 258 may be configured to receive second seal 208. The second seal is configured to prevent and/or limit gas from flowing through the slot. The second seal may have any suitable size(s) or shape(s) to facilitate movement of the adjustment arm but limit and/or prevent gas from flowing through the slot.

Figure 10:
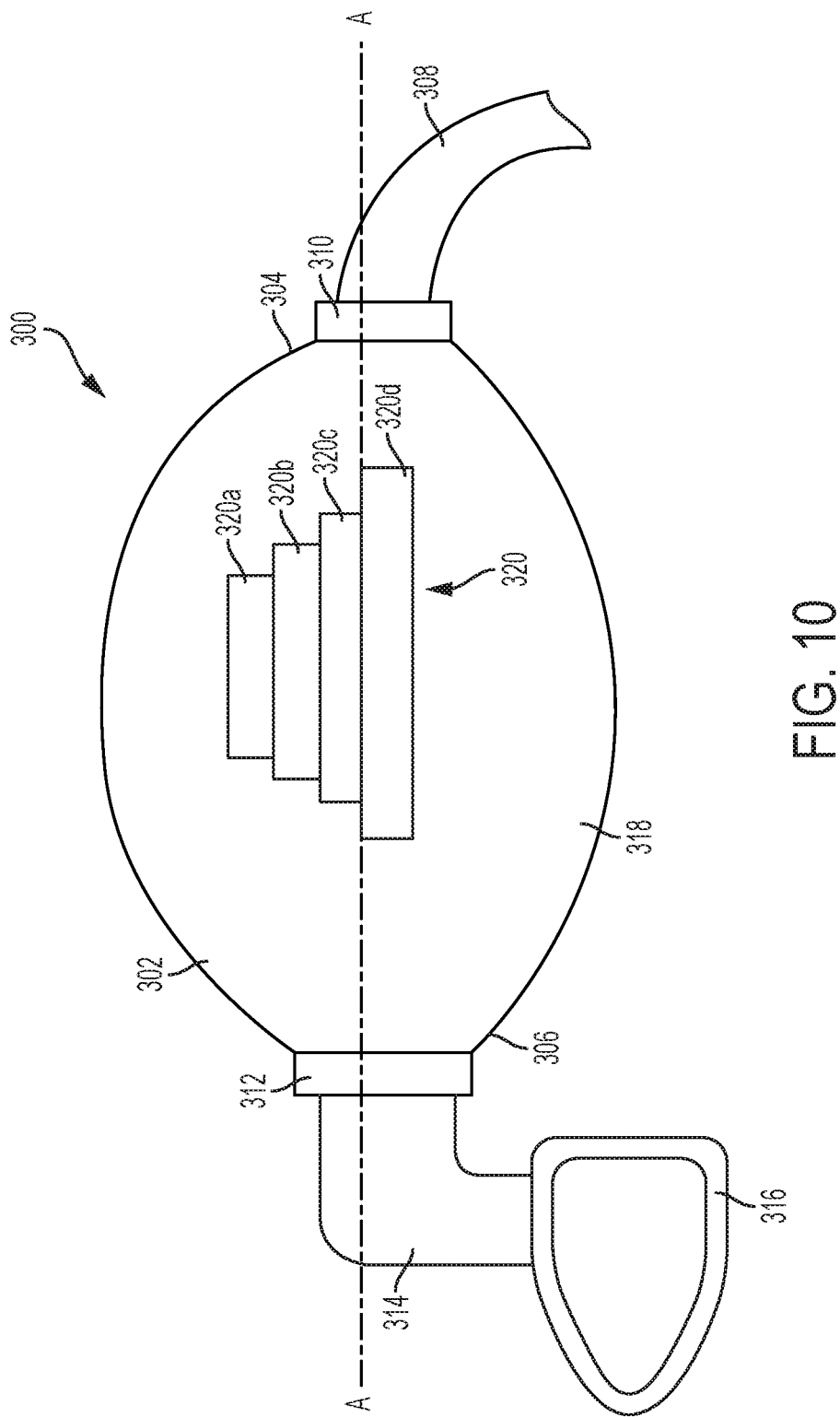
FIG. 10 is a side elevation view of another embodiment of a manual resuscitator regulating system.

FIG. 10 shows an embodiment of a manual resuscitator regulating system, which is generally indicated at 300, according to aspects of the present teachings. FIG. 10 depicts manual resuscitator regulating system 300 including a chamber 302 with a first end 304 and a second end 306, an intake assembly generally indicated at 310, an outtake assembly generally indicated at 312, hosing 308, a mask connector 314, a mask 316, and a placement indicator generally indicated at 320. Most of the features of this embodiment may be the same or similar to one or more embodiments described above and shown in FIGS. 1-9. For example, intake assembly may include a valve housing, a regulator disc, a seal, and a control disc (not shown). In other examples, manual resuscitator regulating system 300 may include more or less components. For example, manual resuscitator regulating system 300 may include an intake assembly and no outtake assembly. In other examples, manual resuscitator regulating system 300 may not include the intake assembly or the outtake assembly.

Placement indicator 320 may be attached to, or formed with, an outer surface 318 of chamber 302. Placement indicator 320 may be configured to guide or indicate to a user where to squeeze or compress the chamber to facilitate the delivery of a selected volume of gas. For example, placement indicator 320 may include indicia corresponding to one or more volumes of gas, such that if a user compresses or squeezes the chamber where indicated, the selected volume of gas may be delivered. In some examples, the placement indicator may be configured to help a user identify where to properly place a user's hand and/or finger(s) on the chamber. This configuration may serve to help limit variations or inconsistency in the volume of gas delivered between different users with different hand size.

Placement indicator 320 may be configured to provide visual, auditory, and/or tactile indicators to a user. For example, the placement indicator may include one or more references, indices, guides, charts, symbols, letters, numbers, colors, and/or codes corresponding with a selected volume of gas and/or patient size. In some examples, the placement indicator may include defined compression zones or areas indicating where to compress to deliver a selected volume of gas and/or for a selected size of patient (e.g. grip chart). In other examples, the placement indicator may include grooves, ribs, projections, teeth, tabs, among others. Additionally, or alternatively, placement indicator 320 may include tabs that are configured to press together to indicate finger and/or hand placement on the chamber. In some examples, the placement indicator may include a groove or recess shaped to receive one or more portions of a user's hand or finger(s).

Placement indicator 320 may be configured to allow a user to selectively move or adjust finger and/or hand placement to a selected volume of gas and/or size of patient. For example, the placement indicator may be configured to allow a user to selectively adjust or vary the user's grip circumferentially in a plane perpendicular to longitudinal axis A. Additionally, or alternatively, the placement indicator may be configured to allow a user to selectively adjust or vary the user's grip longitudinally along longitudinal axis A. The placement indicator may be configured to allow a user to selectively move or adjust finger and/or hand placement in any suitable direction, including vertically, horizontally, and/or diagonally.

Placement indicator 320 may include multiple placements. For example, placement indicator 320 may include a first placement 320a, a second placement 320b, a third placement 320c, and a fourth placement 320d. Although placement indicator 320 depicts four placements, placement indicator 320 may include any suitable number of placements. Placement indicators 320a-d may include one or more references, indices, guides, symbols, letters, numbers, colors, and/or codes. For example, placement indicator 320a may indicate small (or 400 ml), placement indicator 320b may indicate average (or 500 ml), placement indicator 320c may indicate large (or 600 ml), and placement indicator 320d may indicate extra-large (or 700 ml). In other examples, placement indicator 320a may indicate the color purple (or 80 ml), placement indicator 320b may indicate the color yellow (or 105 ml), placement indicator 320c may indicate the color blue (or 160 ml), and placement indicator 320d may indicate orange (or 210 ml).

Although placement indicators 320 *a-d* are shown to be shaped the same, the placement indicators may have any suitable shape(s) and/or sizes. For example, placement indicators 320a-d may each be generally rectangular, as shown in FIG. 10. In other examples, the placement indicators may be cylindrical, triangular, or ovular. In some examples, the placement indicator may be sized to at least partially extend and/or surround the circumference of the chamber, such as a sleeve.

Placement indicator 320 may be configured to attach to, retrofit and/or incorporate with existing manual resuscitators. For example, placement indicator 320 may be configured to be releasably attached, such as a sleeve or wrap. In some examples, the placement indicator may include one or more adhesive materials, snaps, locks, among others. In other examples, the placement indicator may be configured to allow a user to interchange one or more placement indicators.

Additionally, although FIG. 10 depicts manual resuscitator regulating system 300 and/or chamber 302 including one placement indicator 320, manual resuscitator regulating system 300 may include two or more placement indicators. For example, the chamber may include a second placement indicator (not shown) positioned generally opposite from placement indicator 320. In some examples, the second placement indicator may mirror the first placement indicator. The second placement indicator may be configured to complement, correspond and/or facilitate placement indicator 320.

The placement indicator may be in any suitable orientation(s) or position(s). For example, the placement indicator may be oriented to increase visibility of the indicia or other visual information to facilitate placement on the chamber. The placement indicator may include any suitable structure(s) to facilitate visual, tactile, and/or auditory indicators of the placement indicator.

Placement indicator 320 may be used in conjunction with or independently from the intake assembly and/or outtake assembly. For example, the indicia or indicators may be configured to coordinate with and/or complement one or more settings on the outtake assembly and/or intake assembly.

Figure 11:
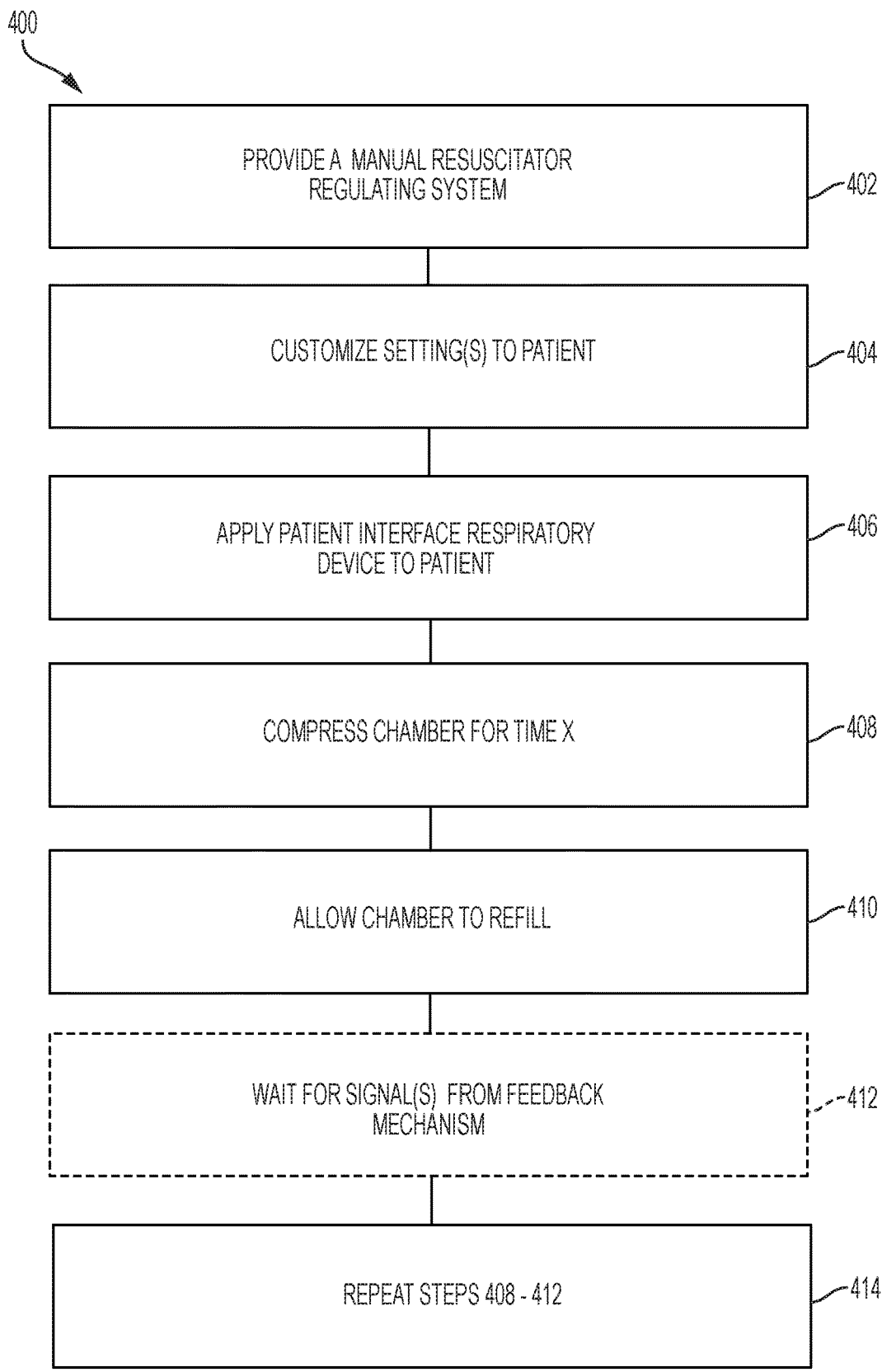
FIG. 11 is a flowchart depicting an exemplary method of operating a manual resuscitator regulating system in accordance with the principles of the present disclosure.

FIG. 11 is a flowchart illustrating steps performed in an exemplary method, and may not recite the complete process or all steps of the process. FIG. 11 depicts multiple steps of a method, generally indicated at 400, which may be performed in conjunction with the manual resuscitator regulating systems according to aspects of the present disclosure. Although various steps of method 400 are described and depicted in FIG. 11, the steps need not necessarily all be performed, and in some cases may be performed in a different order than the order shown.

At step 402, a manual resuscitator regulating system is provided. The manual resuscitator regulating system may include and/or incorporate some or all of the characteristics described above with respect to FIGS. 1-10, such as an intake assembly configured to permit a selected volume of gas to flow over a predetermined amount of time, an outtake assembly configured to permit a selected volume of gas flow over a predetermined amount of time, a chamber, and a patient interface respiratory device configured to deliver gas to the patient. The intake assembly and the outtake assembly may include one or more adjustment mechanisms configured to allow a user to selectively adjust the volume of gas that flows in and out of the chamber. The intake assembly and the outtake assembly may be configured to coordinate with one another to deliver a selected tidal volume and/or volume of gas. The manual resuscitator regulating system may include a feedback mechanism configured to provide one or more signals to a user when to squeeze or compress the chamber. The manual resuscitator regulating system may include a placement indicator configured to indicate or guide a user where to squeeze or compress the chamber. The functions and structures of the various components of the manual resuscitator regulating system also may be as described previously.

At step 404, the setting(s) on the intake assembly and/or the outtake assembly may be customized based on one or more characteristics of a patient to deliver a selected volume of gas to the patient, for example as described above. A user may approximate a patient's age and/or size to determine the customized setting(s) on the intake assembly and/or the outtake assembly. The setting(s) on the intake assembly and the outtake assembly may be customized and/or adjusted to be on the same setting or on different setting(s). For example, a user may adjust the setting on the intake assembly to be on the same setting as the outtake assembly, such as both on the same number, color, code, letter, or alternatively, the user may adjust the setting on the intake assembly to be on a different setting from the outtake assembly. Additionally, or alternatively, the user's finger(s) and/or hand may be positioned on the placement indicator based on selected volume of gas and/or size of patient.

At step 406, the patient interface respiratory device may be applied to the patient. The patient interface respiratory device may include a mask, endotracheal tube, laryngeal mask airway, and/or any other suitable device to deliver gas to a patient.

At step 408, the chamber may be compressed for X amount of time to deliver a selected volume of gas to a patient, for example as described above. In some examples, the chamber may be compressed for approximately 1 second.

At step 410, the chamber may be allowed to refill (or fill) with the selected volume of gas for a predetermined amount of time, for example as described above.

At step 412, the user may wait for one or more signals from a feedback mechanism, for example as described above. In some examples, one or more signals may alert a user five (5) seconds after the chamber began to refill.

At step 414, the user may repeat steps 408 through 412.

Figure 12A:
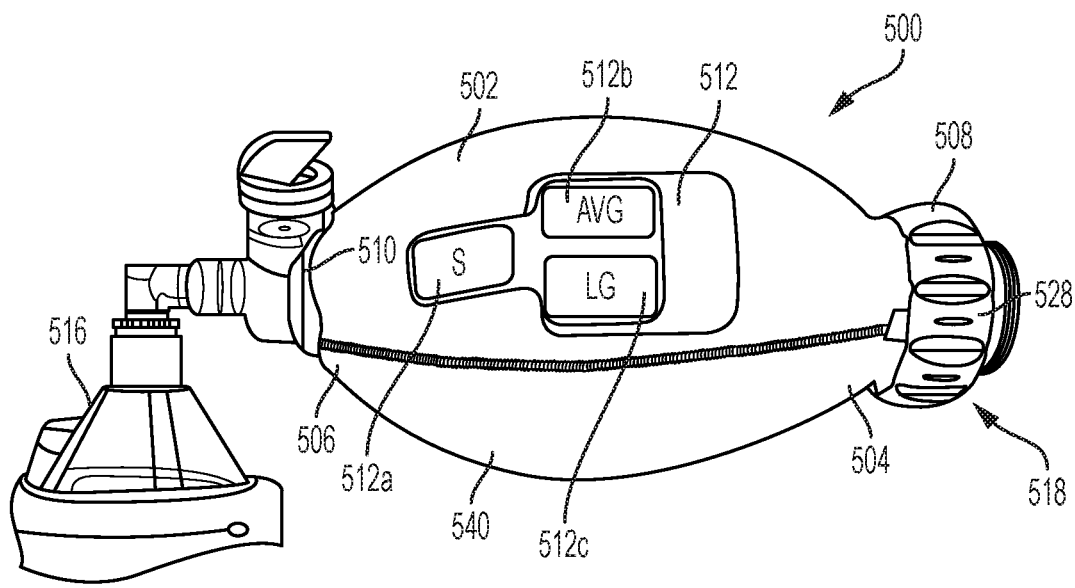
FIGS. 12A-12B is another embodiment of a manual resuscitator regulating system.
Figure 12B:
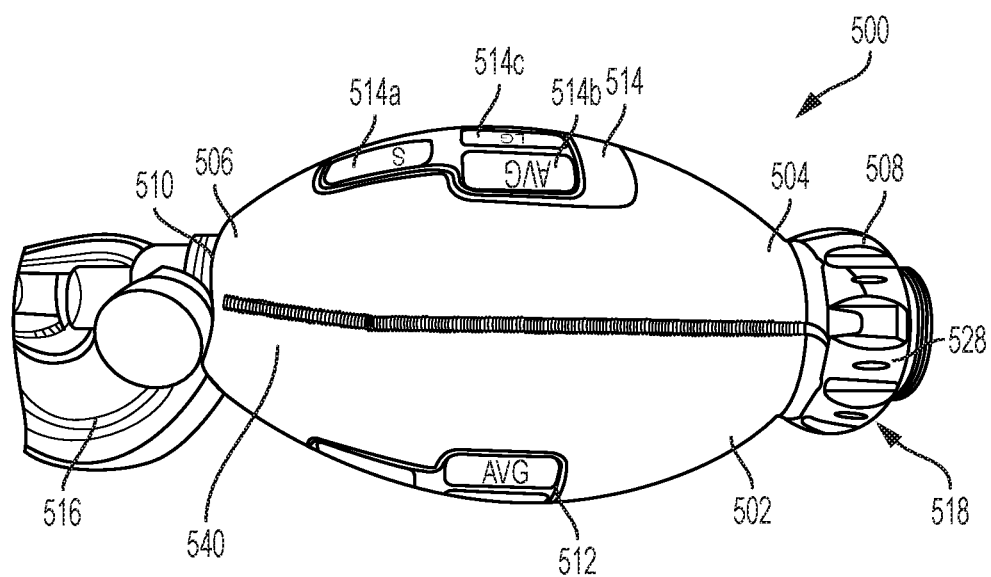

FIGS. 12A and 12B depict another embodiment of a manual resuscitator regulating system, which is generally indicated at 500, according to aspects of the present teachings. FIGS. 12A and 12B depict manual resuscitator regulating system 500 including a chamber 502 with a first end 504 and a second end 506, an intake assembly indicated at 508, an outtake assembly indicated at 510, a first placement indicator 512, a second placement indicator 514, and a patient interface respiratory device 516. Most of the features of this embodiment may be the same or similar to one or more embodiments described above and shown in FIGS. 1-10. For example, manual resuscitator regulating system 500 may include a feedback mechanism configured to provide one or more signals to a user when to squeeze or compress the chamber. Intake assembly 508 includes an adjustment mechanism generally indicated at 518. Outtake assembly 510 may include and/or incorporate a flapper valve or a one-way valve (not shown) to facilitate one-way movement of gas. In other examples, manual resuscitator regulating system 500 may include more or less components. For example, outtake assembly 510 may include an adjustment mechanism configured to coordinate with intake assembly 508 to deliver a selected tidal volume and/or volume of gas.

First placement indicator 512 and second placement indicator 514 are attached to a sleeve 540 disposed circumferentially around chamber 502. Sleeve 540 may be releasably attached to chamber 502 and configured to allow chamber 502 to regain its original shape after a user compresses or squeezes the chamber. Sleeve 540 may be made of one or more suitable materials, such as rubber (neoprene), polymer, elastic, mesh, and/or other materials with resilient properties. In some examples, sleeve 540 may be one or more suitable colors, such as yellow, green, black, and/or orange. In some examples, sleeve 540 may include one or more bright or fluorescent colors or reflective bands for increased visibility. Additionally, or alternatively, the sleeve may be configured to help a user hold and/or support the chamber, such as by including non-slip gripping material and/or a strap that can be engaged by a user's hand(s). Although first and second placement indicators are attached to sleeve 540, first and second placement indicators may be attached to, and/or formed with, an outer surface of chamber 502.

First placement indicator 512 is positioned generally opposite from second placement indicator 514 on the sleeve of chamber 502. The first and second placement indicators are configured to guide and/or indicate to a user where to squeeze or compress the chamber to facilitate the delivery of a selected volume of gas. In some examples, the first and second placement indicators may be configured to deliver a selected volume of gas if a user squeezes or compresses in the defined areas or zones of the first and second placement indicators. Additionally, first and second placement indicators may include tactile feedback or targets configured to provide one or more tactile signals to a user when a selected volume of gas flows out of chamber. For example, when a user squeezes or compresses the first and second placement indicators and a user's fingers and/or hand on the first placement indicator touch and/or are palpable to the user's fingers and/or hand on the second placement indicator, this may signal to a user when a selected volume of gas flows out of chamber. This configuration may indicate to a user when to release the chamber and/or allow the chamber to refill. Although second placement indicator 514 is positioned generally opposite first placement indicator 512, the second placement indicator may be positioned further away from or closer to the first placement indicator. Additionally, although first and second placement indicators are mirror images of the other, first and second placement indicators may be in any suitable orientation or direction.

The first and second placement indicators are configured to allow a user to selectively adjust or vary a user's grip circumferentially and longitudinally in relation to chamber 502 to deliver a selected volume of gas. For example, first placement indicator 512 includes a first placement 512*a* positioned longitudinally in relation to the chamber from a second placement 512*b* and a third placement 512*c*. Second placement 512*b* is positioned circumferentially in relation to the chamber from third placement 512*c*. Although second placement indicator 514 has the same or similar orientation to first placements 512*a-c*, a first placement 514*a*, a second placement 514*b*, and a third placement 514*c* of the second placement indicator may be any suitable direction, including vertically, horizontally, and/or diagonally, to complement, correspond and/or facilitate first placement indicator 512.

Figure 13:
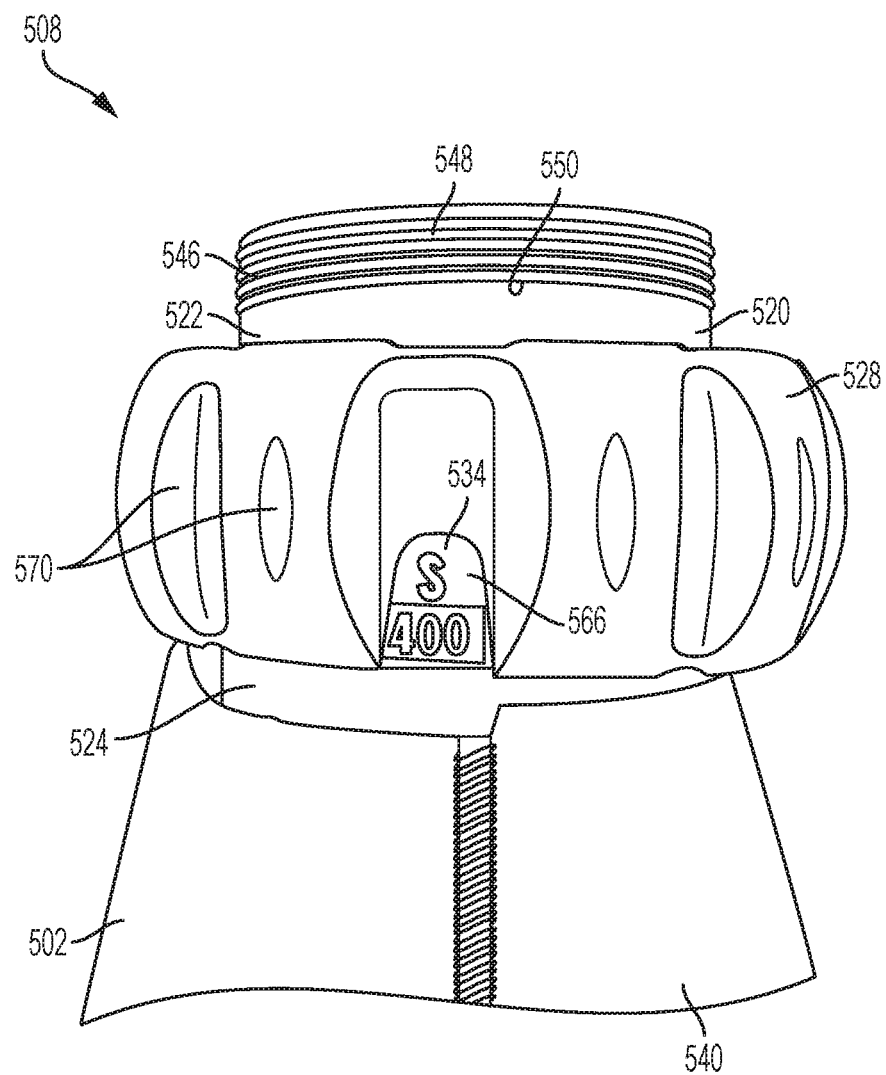
FIG. 13 is a side view of an intake assembly of the manual resuscitator regulating system embodiment of FIGS. 12A-12B.
Figure 14:
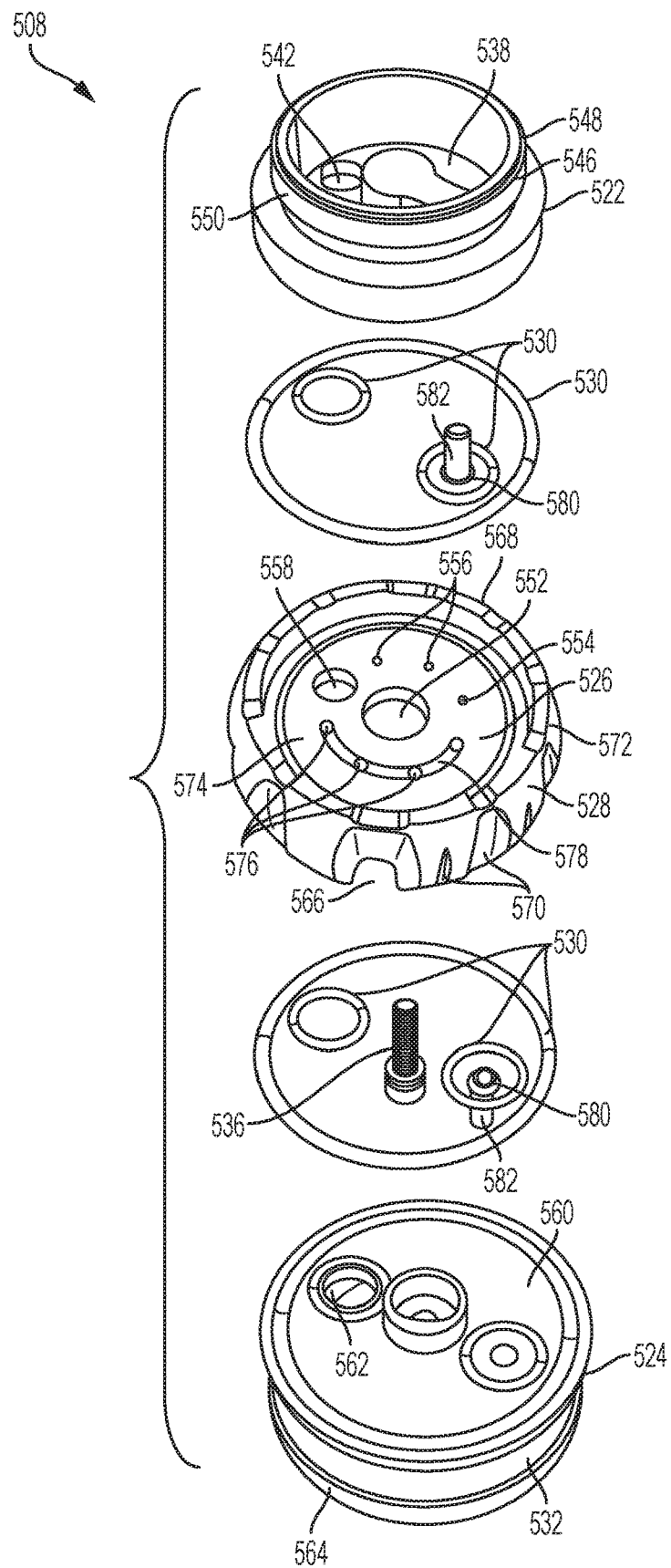
FIG. 14 is an exploded view of the intake assembly of the manual resuscitator regulating system embodiment of FIGS. 12A-12B.

FIGS. 13-14 depict various views of intake assembly 508 of manual resuscitator regulating system 500. FIG. 13 is a side view of intake assembly 508 and depicts a valve housing 520 with a distal portion 522 and a proximate portion 524, and an adjustment collar 528 rotationally connected to valve housing 520. FIG. 14 is an exploded view of intake assembly 508 showing distal portion 522 and proximate portion 524 of the valve housing, adjustment collar 528, and a regulator disc 526. Intake assembly 508 may include one or more features described above and shown in FIGS. 1-10. For example, intake assembly 508 may include a plurality of seals 530 and a fastener 536. Valve housing may include an index 534. Regulator disc 526 may include a central aperture 552, a baseline aperture 554, at least one subsequent aperture 556, and an override aperture 558.

Distal portion 522 of the valve housing includes a body 538, a vent 542, and an attachment extension 546. Distal portion is configured to facilitate movement of air through the valve housing from one or more sources of gas to regulator disc 526. Body may be configured to attach and/or connect to proximate portion 524 of the valve housing. For example, body 538 may be configured to receive and/or retain fastener 536. Vent 542 is configured to facilitate the movement of gas through the distal portion of the valve housing. Attachment extension 546 is configured to removably attach and/or connect to a hose apparatus, tubing apparatus, or other similar structure from one or more sources of gas. The attachment extension includes one or more screw threads 548 on an outer surface 550 of the attachment extension that may engage with complementary screw threads on a hose apparatus, tubing apparatus, or other similar structure. In other embodiments, the attachment extension may be configured to slip-on and/or snap-on a hose apparatus, tubing apparatus, or other similar structure.

Proximate portion 524 of the valve housing includes a body 560, a vent 562, and an attachment extension 564. Proximate portion 524 is configured to facilitate movement of air through the valve housing from regulator disc 526 to chamber 502. Body 560 may be configured to attach and/or connect to distal portion 522 of the valve housing. In some examples, proximate portion 524 may be fixedly attached to, or formed with, distal portion 522.

Proximate portion 524 includes index 534 disposed circumferentially on an outer surface 532 of the proximate portion (see, for example, FIG. 13). Index 534 includes a series of letters, numbers, and colors configured to correspond with the rotational position of regulator disc 526 to indicate a selected volume of gas. For example, an "s" or "small" setting may be configured to be positioned to permit a selected volume of gas (e.g. 400 ml) over a five (5) second period of time, an "avg" or "average" setting may be configured to be positioned to permit a selected volume of gas (e.g. 500 ml) over a five (5) second period of time, and a "lg" or "large" setting may be configured to be positioned to permit a selected volume of gas (e.g. 600 ml) over a five (5) second period of time. In some examples, index 534 may include settings configured for a pediatric patient. Although index 534 includes letters, numbers, and colors, index 534 may include any combination of letters, numbers, colors, or other indicia. Additionally, index 534 may include color-coding schemes (e.g. Broselow-Luten system).

Regulator disc 526 is disposed between distal portion 522 and proximate portion 524 and is fixedly attached to, and/or formed with adjustment collar 528. Distal and proximate portions are configured to facilitate rotational movement of regulator disc 526. The regulator disc may rotate independently of the distal and proximate portions of the valve housing while the distal and proximate portions remain in a fixed position in relation to the regulator disc.

Adjustment collar 528 is configured to facilitate a user to selectively move the adjustment collar to one or more positions or settings to permit a selected volume of gas. The adjustment collar includes a first notch 566 and a second notch 568 configured to expose one or more settings of index 534. Although first notch 566 is positioned generally opposite from second notch 568, the first notch and the second notch may be in any suitable position(s). In some examples, the first notch and second notch may be configured to expose the same indicia on index 534 to facilitate visibility of the indicia. In other examples, the first notch may be configured to expose different indicia than the second notch. The first and second notches may be any suitable shape(s) and size(s) to facilitate visibility of the index. Although the adjustment collar includes two notches, adjustment collar 528 may include one, three, or more notches. Index 534 may include the same indicia in one or more locations on the index to facilitate visibility, such that the same indicia may be visible in two or more notches. In other examples, index 534 may include complementary indicia in one or more locations, such that the complementary indicia may be visible in two or more notches.

Adjustment collar 528 is depicted as including a plurality of grooves or recesses 570 disposed on an outer surface 572 of the adjustment collar. Recesses 570 are configured to facilitate a user to select, adjust, and/or toggle between at least two volume amounts and/or settings on index 534. Recesses 570 may extend generally perpendicular to the rotational direction of the adjustment collar. Recesses 570 may have any suitable shape(s) and size(s). Additionally, adjustment collar 528 may be any suitable color and/or have any suitable structure to facilitate visibility to a user, such as yellow, orange, and/or reflective material.

Intake assembly 508 may include a click stop mechanism 574 for making the adjustment collar stop with a click at any one of a plurality of click stop positions disposed on the regulator disc when the adjustment collar is rotated. This configuration may help a user select, adjust, and/or toggle between volume amounts and/or settings on index 534. The click stop mechanism may be configured to facilitate a spring-biased ball bearing, or similar. For example, click-stop mechanism 574 may include a plurality of depressions 576 which determine the plurality of click stop positions; a ball guide groove 578 formed on the regulator disc, one or more balls 580 positioned at the ball guide groove and configured to engage with, and/or disengage from, the depressions, and one or more pegs 582 configured to support and/or press balls 580 into contact with the click stop positions. Pegs 582 may be made of one or more suitable materials, such as rubber, plastic, and/or other materials with resilient properties.

Figure 15:
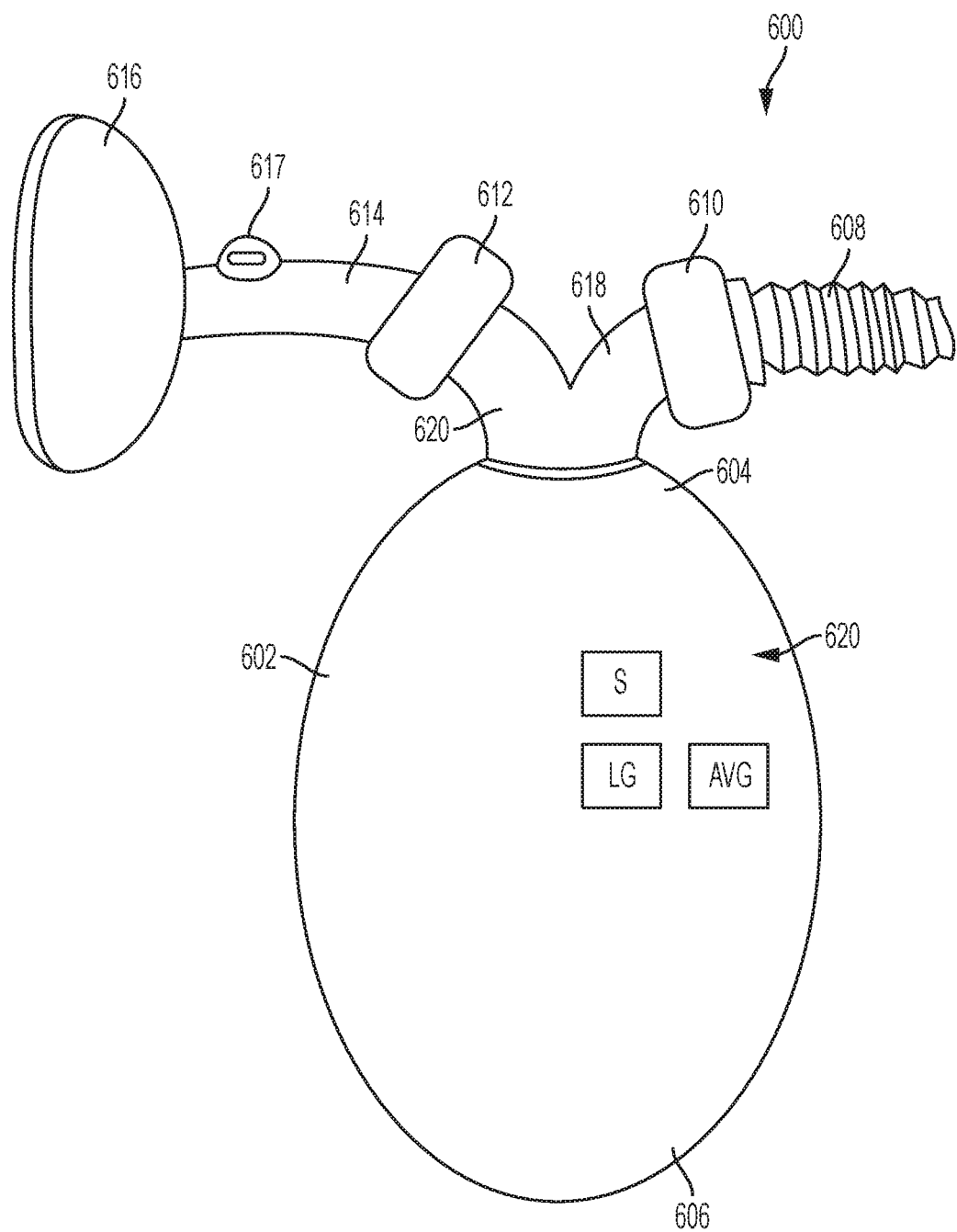
FIG. 15 is a side view of another embodiment of a manual resuscitator regulating system.

FIG. 15 shows another embodiment of a manual resuscitator regulating system, which is generally indicated at 600, according to aspects of the present teachings. FIG. 15 depicts manual resuscitator regulating system 600 including a chamber 602 with a first end 604 and a second end 606, an intake assembly generally indicated at 610, an outtake assembly generally indicated at 612, hosing 608, a mask connector 614, a mask 616, a valve 617, and a placement indicator generally indicated at 620. Most of the features of this embodiment may be the same or similar to one or more embodiments described above and shown in FIGS. 1-14. For example, placement indicator may include multiple placements indicating small (or "S"), average (or "AVG"), and large (or "LG") settings. In some examples, intake assembly and/or outtake assembly may include a valve housing, a regulator disc, a seal, a control disc, an adjustment arm, and/or an adjustment collar (not shown). In other examples, manual resuscitator regulating system 600 may include more or less components. For example, manual resuscitator regulating system 600 may include an intake assembly and no outtake assembly.

As shown in FIG. 15, intake assembly 610 and outtake assembly 612 are operably connected and/or attached to first end 604 of the chamber. Intake assembly 610 is operably connected and/or attached to the chamber through an intake hose 618. Outtake assembly 612 is operably connected and/or attached the chamber through an outtake hose 620. Intake hose 618 may partially form with and/or attach to outtake hose 620. In other examples, intake hose 618 may be structurally separate from outtake hose 620. Although manual resuscitator regulating system 600 depicts the intake assembly and outtake assembly operably connected and/or attached to the chamber through intake hose 618 and outtake hose 620, manual resuscitator regulating system 600 may include any suitable structure to connect and/or attach the intake assembly and/or outtake assembly to the chamber.

While embodiments of one or more manual resuscitator regulating systems have been particularly shown and described, many variations may be made therein. This disclosure may include one or more independent or interdependent embodiments directed to various combinations of features, functions, elements and/or properties. Other combinations and sub-combinations of features, functions, elements and/or properties may be claimed later in a related application. Such variations, whether they are directed to different combinations or directed to the same combinations, whether different, broader, narrower or equal in scope, are also regarded as included within the subject matter of the present disclosure. Accordingly, the foregoing embodiments are illustrative, and no single feature or element, or combination thereof, is essential to all possible combinations that may be claimed in this or a later application.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the invention(s) includes all novel and nonobvious combinations and subcombinations of the various elements, features, functions, and/or properties disclosed herein. Similarly, where any claim recites "a" or "a first" element or the equivalent thereof, such claim should be understood to include incorporation of one or more such elements, neither requiring nor excluding two or more such elements. Furthermore, any aspect shown or described with reference to a particular embodiment should be interpreted to be compatible with any other embodiment, alternative, modification, or variance.

The following is a list of applicable reference numbers, along with descriptions of each numbered component:

| Ref. No. | Description |
| --- | --- |
| 10 | Manual resuscitator regulating system |
| 12 | Intake Assembly |
| 14 | Outtake Assembly |
| 16 | Chamber |
| 18 | Feedback Mechanism |
| 20 | Patient Interface Respiratory Device |
| 100 | Manual resuscitator regulating system |
| 102 | Chamber |
| 104 | Intake Assembly |
| 106 | Outtake Assembly |
| 108 | First end of chamber |
| 110 | Second end of chamber |
| 112 | Gas Connector |
| 114 | Hosing |
| 116 | Mask |
| 118 | Mask Connector |
| 120 | Valve Housing |
| 122 | Regulator Disc |
| 124 | Seal |
| 126 | Control Disc |
| 128 | Inner Surface of valve housing |
| 130 | Outer Surface of valve housing |
| 132 | Opening of valve housing |
| 134 | Attachment Member |
| 136 | Central Aperture of regulator disc |
| 138 | Body of regulator disc |
| 140 | Annular Collar of attachment member |
| 142 | Distal End of attachment member |
| 144 | Baseline Aperture |
| 146 | Subsequent Aperture |
| 148 | Override Aperture |
| 150 | Body of control disc |
| 152 | Protrusion |
| 154 | Vent |
| 156 | Adjustment Arm |
| 158 | Teeth |
| 160 | Internal surface of annular collar |
| 162 | Complementary Teeth on protrusion |
| 164 | Index |
| 166 | Slot on valve housing |
| 200 | Outtake Assembly |
| 202 | Valve Housing |
| 204 | Regulator Disc |
| 206 | First Seal |
| 208 | Second Seal |
| 210 | Control Disc |
| 212 | Fastener |
| 214 | Inner surface of valve housing |
| 216 | Outer surface of valve housing |
| 217 | Body of Regulator Disc |
| 218 | Attachment member |
| 220 | Baseline Aperture |
| 222 | Subsequent Aperture |
| 224 | Override Aperture |
| 226 | Opening |
| 228 | Slotted Groove |
| 230 | Annular collar |
| 232 | Distal end |
| 234 | Teeth |
| 236 | Outer surface of annular collar |
| 238 | Complementary teeth |
| 240 | Complementary apertures |
| 242 | Central aperture |
| 244 | Body of control disc |
| 246 | Central hole |
| 248 | Vent |
| 250 | Adjustment arm |
| 252 | Protuberance |
| 254 | Longitudinal recess |
| 256 | Notch |
| 258 | Slot |
| 300 | Manual resuscitator regulating system |
| 302 | Chamber |
| 304 | First end |
| 306 | Second end |
| 308 | Hosing |
| 310 | Intake assembly |
| 312 | Outtake assembly |
| 314 | Mask connector |
| 316 | Mask |
| 318 | Outer surface of chamber |
| 320 | Placement indicator |
| 320a | First placement |
| 320b | Second placement |
| 320c | Third placement |
| 320d | Fourth placement |
| 400 | Method |
| 500 | Manual resuscitator regulating system |
| 502 | Chamber |
| 504 | First end |
| 506 | Second end |
| 508 | Intake assembly |
| 510 | Outtake assembly |
| 512 | First placement indicator |
| 512a | First placement |
| 512b | Second placement |
| 512c | Third placement |
| 514 | Second placement indicator |
| 514a | First placement |
| 514b | Second placement |
| 514c | Third placement |
| 516 | Patient interface respiratory device |
| 518 | Adjustment mechanism |
| 520 | Valve housing |
| 522 | Distal portion |
| 524 | Proximate portion |

-continued

| Ref. No. | Description |
| --- | --- |
| 526 | Regulator disc |
| 528 | Adjustment collar |
| 530 | Seals |
| 532 | Outer surface (of proximate portion) |
| 534 | Index |
| 536 | Fastener |
| 538 | Body (of distal portion) |
| 540 | Sleeve |
| 542 | Vent (of distal portion) |
| 546 | Attachment extension (of distal portion) |
| 548 | Screw threads |
| 550 | Outer surface (of attachment extension 546) |
| 552 | Central aperture |
| 554 | Baseline aperture |
| 556 | Subsequent apertures |
| 558 | Override aperture |
| 560 | Body (of proximate portion) |
| 562 | Vent (of proximate portion) |
| 564 | Attachment extension (of proximate portion) |
| 566 | First notch |
| 568 | Second notch |
| 570 | Recesses |
| 572 | Outer surface of adjustment collar |
| 574 | Click stop mechanism |
| 576 | Depressions |
| 578 | Ball guide groove |
| 580 | Balls |
| 582 | Pegs |
| 600 | Manual resuscitator regulating system |
| 602 | Chamber |
| 604 | First end |
| 606 | Second end |
| 608 | Hosing |
| 610 | Intake assembly |
| 612 | Outtake assembly |
| 614 | Mask connector |
| 616 | Mask |
| 617 | Valve |
| 618 | Intake hose |
| 620 | Outtake hose |

We claim:

1. A manual resuscitator regulating system comprising:
a compressible chamber having a flexible wall, the flexible wall of the chamber having a first grip placement indicator and a second grip placement indicator configured to guide a user where to grip the chamber depending on an age or size of a patient, the first grip placement indicator being configured to deliver a first pre-set volume of air to a first patient by manually compressing the first grip placement indicator to a point where opposing portions of the flexible wall come into contact, and the second grip placement indicator being configured to deliver a second pre-set volume of air to a second patient by manually compressing the second grip placement indicator to a point where opposing portions of the flexible wall come into contact,
an intake assembly attached to the chamber and configured to permit air flow into the chamber at a first pre-set in-flow rate and a second pre-set in-flow rate; and
an outtake assembly attached to the chamber and configured to permit air to flow out of the chamber when the chamber is properly gripped on the grip placement indicators,
wherein the intake assembly comprises a first index and a second index, the first index corresponding to the first pre-set flow rate and to the first patient's size or age, and the second index corresponding to the second pre-set flow rate and the second patient's age or size,
wherein the intake assembly, set to the first index, allows intake of the first pre-set volume over a first time period equal to a time period between a completed manual compression of the first grip placement indicator and a manually sensed signal to the user that the chamber has completely refilled and should be recompressed,
wherein the intake assembly, set to the second index, allows intake of the second pre-set volume over a second time period equal to a time period between a completed manual compression of the second grip placement indicator and a manually sensed signal to the user that the chamber has completely refilled and should be recompressed, and
wherein the first patient's size or age is larger or older than the second patient's size or age, the first pre-set volume being greater than the second pre-set volume, and the first pre-set in-flow rate being greater than the second pre-set in flow rate.

2. The manual resuscitator regulating system of claim 1, wherein the intake assembly is adjustable to change between pre-set in-flow rates.

3. The manual resuscitator regulating system of claim 2, wherein the intake assembly and the outtake assembly are configured to coordinate with each other to deliver pre-set volume of air to the patient.

4. The manual resuscitator regulating system of claim 1, wherein each grip placement indicator is configured to deliver a selected tidal volume.

5. The manual resuscitator regulating system of claim 1, wherein the outtake assembly includes one or more adjustment mechanisms configured to allow the user to selectively adjust a volume of air flow out of the chamber.

6. The manual resuscitator regulating system of claim 5, wherein the one or more adjustment mechanisms have coordinated indicia to facilitate desired relative air flow between the intake and outtake assemblies.

7. The manual resuscitator regulating system of claim 6, wherein the coordinated indicia are color coordinated.

8. The manual resuscitator regulating system of claim 1, wherein each of the first and second time periods between compressions is at least three seconds.

9. The manual resuscitator regulating system of claim 1, wherein (a) manually sensed contact between portions of the flexible wall associated with the first and second grip placement indicators is configured to provide a first manually sensed signal to the user that a tidal volume of air has been delivered to the first or second patient, and therefore manual compression of the compressible chamber should be released permitting the chamber to refill with air, and (b) manually sensed complete refill of the compressible chamber, manually sensed by the user's hand feeling that outward expansion pressure of the compressible chamber exerted on the user's hand has stopped, and is configured to provide a second manually sensed signal to the user that a safe and effective time interval between compressions has passed, and that the compressible chamber should be manually compressed again until manually sensing the first signal again, wherein the first and second manually sensed signals together guide the user to administer a volume of air per compression, a rate of compression, and a volume of air over an extended resuscitation period.

10. The manual resuscitator regulating system of claim 9, wherein the intake assembly is a first intake assembly, and further comprising:

an override aperture selectable to disable the first intake assembly and allow an air flow rate higher than each of the first and second pre-set in-flow rates into the compressible chamber.

11. The manual resuscitator regulating system of claim 10, wherein the first intake assembly allows the compressible chamber to refill in more than three seconds, the override aperture allowing the compressible chamber to refill in less than three seconds.

12. The manual resuscitator regulating system of claim 1, wherein the first and second pre-set volumes are tidal volumes for the first and second patients, respectively.

13. The manual resuscitator regulating system of claim 1, wherein the intake assembly and the outtake assembly are attached to opposite sides of the chamber.

14. The manual resuscitator regulating system of claim 1, wherein the intake assembly and the outtake assembly are attached on a same side of the chamber.

15. The manual resuscitator regulating system of claim 2, further comprising:
a manual feedback mechanism configured to provide manually sensed, non-visual signals to the user to regulate a manual compression rate of the chamber.

16. The manual resuscitator regulating system of claim 15, wherein the manual resuscitator regulating system includes a third placement indicator and a fourth placement indicator for delivering different volumes of air per compression.

17. The manual resuscitator regulating system of claim 16, wherein the first grip placement indicator and the second grip placement indicator are mirror images of each other, and are configured to coordinate with each other to permit the pre-set volume of air to flow out of the chamber.

18. The manual resuscitator regulating system of claim 16, wherein the first grip placement indicator and the second grip placement indicator includes a tactile target configured to provide tactile signals to the user when the pre-set volume of air flows out of the chamber.

19. The manual resuscitator regulating system of claim 15, wherein the first grip placement indicator is configured to allow the user to selectively move hand placement longitudinally along a longitudinal axis of the chamber.

20. The manual resuscitator regulating system of claim 19, wherein the first grip placement indicator is oriented circumferentially around the chamber.

* * * * *